US007270960B2

(12) United States Patent
Hellstrom et al.

(10) Patent No.: US 7,270,960 B2
(45) Date of Patent: Sep. 18, 2007

(54) DIAGNOSIS OF OVARIAN CARCINOMAS

(75) Inventors: Ingegerd Hellstrom, Seattle, WA (US); Jeffrey A. Ledbetter, Shoreline, WA (US); Martha Hayden-Ledbetter, Shoreline, WA (US)

(73) Assignee: Pacific Northwest Research Institute, Seattle, WA (US)

( * ) Notice: Subject to any disclaimer, the term of this patent is extended or adjusted under 35 U.S.C. 154(b) by 478 days.

(21) Appl. No.: 10/233,150

(22) Filed: Aug. 28, 2002

(65) Prior Publication Data

US 2003/0108965 A1    Jun. 12, 2003

Related U.S. Application Data

(60) Provisional application No. 60/316,537, filed on Aug. 29, 2001.

(51) Int. Cl.
G01N 33/48    (2006.01)
G01N 33/50    (2006.01)
G01N 33/53    (2006.01)

(52) U.S. Cl. .......................... 435/7.1; 436/63; 436/64; 436/504

(58) Field of Classification Search .................. None
See application file for complete search history.

(56) References Cited

U.S. PATENT DOCUMENTS

2002/0182619 A1* 12/2002 Lillie et al. .................... 435/6

FOREIGN PATENT DOCUMENTS

| EP | 0 440 321 B1 | 8/1991 |
|---|---|---|
| EP | 1 033 401 A2 | 9/2000 |
| WO | WO 00/50900 | 8/2000 |
| WO | WO 00/77191 A1 | 12/2000 |
| WO | WO01/16354 * | 3/2001 |
| WO | WO 01/16354 A1 | 3/2001 |
| WO | WO 01/59064 A2 | 8/2001 |
| WO | WO 02/00677 | 1/2002 |
| WO | WO 02/071928 A2 | 9/2002 |

OTHER PUBLICATIONS

Clark (Protein Engineering of Antibody Molecules for Prophylactic and Therapeutic Applications in Man, 1993, p. 1).*
Abstract of Cinader, Medical Clinics of North America, 1972, vol. 56, pp. 801-836.*
Hough et al (Cancer Research, 2000, vol. 60, pp. 6281-6287).*
Bingle et al, Oncogene, 2002, vol. 21, pp. 2768-2773.*
Freshney, The Culture of Animal Cells, 1994, p. 5, under the heading "Major Differences in Vitro" and pp. 349-350.*
Scholler et al (PNAS, 1999, vol. 96, pp. 11531-11536).*
Paul, Fundamental Immunology, (text), 1993, pp. 1157-1170.*
Allum. W. et al., "Monoclonal Antibodies in the Diagnosis and treatment of Malignant Conditions." *Surg. Ann.* 18:41-64. 1986.

Bast. R. et al., "A Radioimmunoassay using a Monoclonal Antibody to Monitor the Course of Epithelial Ovarian Cancer." *N. Eng. J. Med.* 309(15):883-887. Oct. 1983.
Bingle. L. et al., "The Putative Ovarian Tumor Marker Gene HE4 (WFDC2). is Expressed in Normal Tissues and Undergoes Complex Alternative Splicing to Yield Multiple Protein Isoforms." *Oncogene* 21:2768-2773. Jan. 2002.
Bell. R. et al., "The Performance of Screening Tests for Ovarian Cancer: Results of a Systematic Review." *Br. J. Obstet. Gynaecol.* 105(11):1136-1147. Nov. 1998.
Burdon. T. et al., "Over-Expression of an Endogenous Milk Protein Gene in Transgenic Mice is Associated with Impaired Mammary Alveolar Development and a *Milchlos* Phenotype." *Mechanisms Dev.* 36:67-74. 1991.
Chang. K. et al., " Molecular Cloning of Mesothelin. a Differentiation Antigen Present on Mesothelium. Mesotheliomas. and Ovarian Cancers." *Proc. Natl. Acad. Sci. USA* 93:136-140. Jan. 1996.
Chang. K. et al., "Frequent Expression of the Tumor Antigen CAK1 in Squamous-Cell Carcinomas," *Int. J. Cancer* 51:548-554. 1992.
Chang. K. et al., "Isolation and Characterization of a Monoclonal Antibody. K1. Reactive with Ovarian Cancers and Normal Mesothelium," *Int. J. Cancer* 50:373-381, 1992.
Chang, K. et al., "Characterization of the Antigen (CAK1) Recognized by Monoclonal Antibody K1 Present on Ovarian Cancers and Normal Mesothelium." *Cancer Research* 50(1):181-186. Jan. 1992.
Chowdhury. P. et al., "Isolation of a High-Affinity Stable Single-Chain Fv Specific for Mesothelin from DNA-Immunized Mice by Phage Display and Construction of a Recombinant Immunotoxin with Anti-tumor Activity." *Proc. Natl. Acad. Sci. USA* 95:669-674. Jan. 1998.
Cioffi. M. et al., "OVCA (CA125) Second Generation" Technical Aspects and Serum Levels in Controls, Patients with Liver Disease, Pregnant Women and Patients with Ovarian Disease. *Tumori* 83(2):594-598, Mar.-Apr. 1997.
Dandekar. A. et al., "Complete Sequence Analysis of cDNA Clones Encoding Rat Whey Phosphoprotein: Homology to a Protease Inhibitor," *Proc. Natl. Acad. Sci. USA* 79(13):3987-3991. Jul. 1982.
Gebauer. G. et al., "Timor Market Concentrations in Normal and Malignant Tissues of Colorectal Cancer Patients and Their Prognostic Relevance." *Anticanc. Res.* 17(4B):2939-2942. Jul.-Aug. 1997.

(Continued)

*Primary Examiner*—Karen A. Canella
(74) *Attorney, Agent, or Firm*—Duane Morris LLP

(57) ABSTRACT

The invention is directed to compositions and methods for the detection of a malignant condition, and relates to the discovery of soluble and cell surface forms of HE4a polypeptides, including HE4a that is overexpressed in ovarian carcinomas. In particular the invention provides a nucleic acid sequence encoding HE4a, and also provides a method of screening for the presence of a malignant condition in a subject by detecting reactivity of an antibody specific for a HE4a polypeptide with a molecule naturally occurring in soluble and/or cell surface form in a sample from such a subject, and by hybridization screening using an HE4a nucleotide sequence, as well as other related advantages.

42 Claims, 6 Drawing Sheets

OTHER PUBLICATIONS

Grütter, M. et al., "The 2.5 Å X-Ray Crystal Structure of the Acid-Stable Proteinase Inhibitor from Human Mucous Secretions analysed in its Complex with Bovine α-Chymotrypsin." *EMBO* 7(2):345-351. Feb. 1988.

Hagiwara. k. et al.. "Mouse SWAM1 and SWAM2 are Antibacterial Proteins Composed of a Single Whey Acidic Protein Motif." *J. Immunol..* 170(4):1973-1979. 2003.

Heinzel. R. et al., "Molecular Cloning and Expression of cDNA for Human Antileukoprotease from Cervix Uteri," *Eur. J. Biochem.* 160(1):61-67. Oct. 1986.

Hellström, I. et al.. "Overexpression of HER-2 in Ovarian Carcinomas." *Cancer Res.* 61:2420-2423, Mar. 2001.

Hirokawa, S. et al., "Neuroblastoma in an Adult with a High Serum Level of Carbohydrate Antigen, CA125: Report of a Case." *Surg. Today* 28:349-354. 1998.

Hough, C. et al., "Large-Scale Serial Analysis of Gene Expression Reveals Genes Differentially Expressed in Ovarian Cancer." *Cancer Res.* 60:6281-6287. Nov. 2001.

Ind, T. et al., "Serum Concentrations of Cancer Antigen 125. Placental Alkaline Phosphatase. Cancer-Associated Serum Antigen and Free Beta Human Chorionic Gonadotrophin as Prognostic Marker for Epithelial Ovarian Cancer," *Br. J. Obstet. Gynaecol.* 104(9):1024-1029. Sep. 1997.

Kirchhoff. C. et al., "A Major Human Epididymis-Specific cDNA encodes a Protein with Sequence Homology to Extracellular Proteinase Inhibitors." *GenBank Accession # X63187*. Dec. 1991.

Kirchhoff. C. et al., "A Major Human Epididymis-Specific cDNA encodes a Protein with Sequence Homology to Extracellular Proteinase Inhibitors." *Biol. Reprod.* 45(2):350-357. Aug. 1991.

Kojima. T. et al.. "Molecular Cloning and Expression of Megakaryocyte Potetiating Factor cDNA." *J. Biol. Chem.* 270(37):21984-21990. Sep. 1995.

Kudoh. K. et al.. "Preoperative Determination of Several Serum Tumor Markers in Patient with Primary Epithelial Ovarian Carcinoma." *Gynaecol. Obstet. Invest.* 47(1):52-57. Jan. 1999.

Larsen. M. et al.. "Molecular Cloning and Expression of ps20 Growth inhibitor." *J. of Biol. Chem.* 273(8):4574-4584. Feb. 1998.

Lloyd, K. et al., " Isolation and Characterization of Ovarian Cancer Antigen CA 125 Using a New Monoclonal Antibody (VK-8): Identification as a Mucin-Type Molecule." *Int. J. Cancer* 71:842-850, 1997.

Meier, W. et al., "Significance of Tumor Marker Determinations in the Primary Therapy of Ovarian Cancer," *Anticancer Res.* 17(4B):2949-2952. Jul.-Aug. 1997.

Meier, W. et al., "CA125 Based Diagnosis and Therapy in Recurrent Ovarian Cancer." *Anticancer Res.* 17(4B):3019-3020, Jul.-Aug. 1997.

Meier. W. et al.. Prognostic Significance of CA125 in Patients with Ovarian Cancer and Secondary Debulking Surgery. *Anticancer Res.* 17(4B):2945-2948. Jul.-Aug. 1997.

Moore. E. et al., Clinical Utility of CA125 Levels in Predicting Laparoscopically Confirmed Salpingitis in Patients with Clinically Diagnosed Pelvic Inflammatory Disease. *Infect. Dis. Obstet. Gynaec.* 6:182-185, 1998.

Papsidero, I . . . "Recent Progress in the Immunological Monitoring of Carcinomas Using Monoclonal Antibodies." *Semin. Surg. Oncol.* 1(4):171-181. 1985.

Sarandakou. A. et al.. "Tumor-Associated Antigens CEA, CA125. SCC and TPS in Gynaecological Cancer." *Eur. J. Gynaecol. Oncol.* 19:73-77. 1998.

Sarandakou, A.. et al., "Vaginal Fluid Serum CEA. CA125 and SCC in Normal Conditions and in Benign and Malignant Diseases of the Genital Tract." *Acta Oncol.* 36(7):755-759. 1997.

Schmandt. R. et al.. "Differential Expression of the Secreted Protease Inhibitor. HE4. in Epithelial Ovarian Cancer," *Gynecologic Oncology* 80(2):319. Feb. 2001.

Scholler. N. et al.. "Soluble Member(s) of the Mesothelin/ Megakaryocyte Potentiating Factor Family are Detectable in Sera from Patients with Ovarian Carcinoma." *Proc. Natl. Acad. Sci. USA* 96:11531-11536. Sep. 1999.

Schummer. M. et al.. "Comparative Hybridization of an Array of 21 500 Ovarian cDNAs for the Discovery of Genes Overexpressed in Ovarian Carcinomas." *Gene* 238(2):375-385. Jul. 1999.

Wang. K. et al.. "Monitoring Gene Expression Profile Changes in Ovarian Carcinomas Using cDNA Microarray," *Gene* 299(1-2):101-108. Mar. 1999.

Wiedow, O. et al.. "Elafin: An Elastase-Specific Inhibitor of Human Skin." *J. Biol. Chem.* 265(25):14791-14795. Sep. 1990.

Yamaguchi. N. et al., "A Novel Cytokine Exhibiting Megakaryocyte Potentiating Activity from a Human Pancreatic Tumor Cell Line HPC-Y5." *J. Biol. Chem.* 269(2):805-808. Jan. 1994.

* cited by examiner

Fig. 4

Plate 1

|   | 1 | 2 | 3 | 4 | 5 | 6 | 7 | 8 | 9 | 10 | 11 | 12 |
|---|---|---|---|---|---|---|---|---|---|----|----|----|
| A | 0.181 | 0.130 | 0.192 | 0.140 | 0.159 | 0.135 | 0.130 | 0.164 | 0.139 | 0.108 | 0.142 | 0.138 |
| B | 0.160 | 0.129 | 0.133 | 0.144 | 0.144 | 0.121 | 0.136 | 0.130 | 0.131 | 0.120 | 0.138 | 0.150 |
| C | 0.147 | 0.146 | 0.130 | 0.158 | 0.135 | 0.142 | 0.139 | 0.121 | 0.130 | 0.113 | 0.118 | 0.146 |
| D | 0.200 | 0.141 | 0.145 | 0.158 | 0.149 | 0.114 | 0.165 | 0.148 | 0.129 | 0.140 | 0.130 | 0.167 |
| E | 0.175 | 0.130 | 0.143 | 0.111 | 0.132 | 0.129 | 0.140 | 0.143 | 0.126 | 0.134 | 0.139 | 0.172 |
| F | 0.154 | 0.122 | 0.133 | 0.133 | 0.135 | 0.144 | 0.161 | 0.132 | 0.117 | 0.121 | 0.118 | 0.182 |
| G | 0.180 | 0.166 | 0.147 | 0.143 | 0.133 | 0.126 | 0.167 | 0.125 | 0.149 | 0.142 | 0.138 | 0.156 |
| H | 0.178 | 0.152 | 0.160 | 0.149 | 0.163 | 0.142 | 0.166 | 0.168 | 0.144 | 0.125 | 0.140 | 0.166 |

Plate 2

|   | 1 | 2 | 3 | 4 | 5 | 6 | 7 | 8 | 9 | 10 | 11 | 12 |
|---|---|---|---|---|---|---|---|---|---|----|----|----|
| A | 0.173 | 0.141 | 0.156 | 0.152 | 0.111 | 0.145 | 0.159 | 0.250 | 0.111 | 0.119 | 0.129 | 0.146 |
| B | 0.158 | 0.129 | 0.128 | 0.124 | 0.135 | 0.108 | 0.112 | 0.154 | 0.138 | 0.101 | 0.103 | 0.135 |
| C | 0.096 | 0.160 | 0.125 | 0.104 | 0.102 | 0.165 | 0.105 | 0.135 | 0.123 | 0.096 | 0.097 | 0.107 |
| D | 0.099 | 0.101 | 0.115 | 0.121 | 0.104 | 0.101 | 0.123 | 0.123 | 0.117 | 0.127 | 0.115 | 0.137 |
| E | 0.108 | 0.130 | 0.143 | 0.101 | 0.113 | 0.118 | 0.140 | 0.107 | 0.097 | 0.136 | 0.102 | 0.131 |
| F | 0.086 | 0.118 | 0.170 | 0.116 | 0.113 | 0.128 | 0.101 | 0.111 | 0.120 | 0.113 | 0.087 | 0.129 |
| G | 0.108 | 0.094 | 0.127 | 0.130 | 0.147 | 0.132 | 0.118 | 0.114 | 0.123 | 0.114 | 0.110 | 0.119 |
| * H | 0.108 | 0.121 | 0.133 | 0.130 | (1.087) 2H5 | 0.139 | 0.107 | 0.116 | 0.124 | 0.106 | 0.138 | 0.143 |

Plate 3

|   | 1 | 2 | 3 | 4 | 5 | 6 | 7 | 8 | 9 | 10 | 11 | 12 |
|---|---|---|---|---|---|---|---|---|---|----|----|----|
| A | 0.152 | 0.166 | 0.126 | 0.153 | 0.128 | 0.122 | 0.138 | 0.116 | 0.140 | 0.092 | 0.119 | 0.172 |
| B | 0.153 | 0.110 | 0.103 | 0.132 | 0.115 | 0.103 | 0.085 | 0.102 | 0.142 | 0.101 | 0.098 | 0.108 |
| C | 0.135 | 0.113 | 0.108 | 0.118 | 0.105 | 0.156 | 0.129 | 0.090 | 0.106 | 0.120 | 0.105 | 0.122 |
| * D | 0.133 | 0.121 | 0.137 | 0.112 | 0.126 | 0.130 | 0.148 | (1.044) 3D8 | 0.116 | 0.133 | 0.127 | 0.130 |
| E | 0.117 | 0.123 | 0.137 | 0.132 | 0.132 | 0.096 | 0.119 | 0.132 | 0.102 | 0.112 | 0.098 | 0.105 |
| F | 0.118 | 0.125 | 0.121 | 0.128 | 0.133 | 0.114 | 0.109 | 0.111 | 0.113 | 0.084 | 0.108 | 0.143 |
| G | 0.147 | 0.139 | 0.131 | 0.121 | 0.108 | 0.097 | 0.137 | 0.118 | 0.106 | 0.132 | 0.101 | 0.110 |
| H | 0.155 | 0.116 | 0.193 | 0.105 | 0.144 | 0.128 | 0.125 | 0.102 | 0.149 | 0.129 | 0.128 | 0.116 |

Plate 4

|   | 1 | 2 | 3 | 4 | 5 | 6 | 7 | 8 | 9 | 10 | 11 | 12 |
|---|---|---|---|---|---|---|---|---|---|----|----|----|
| A | 0.128 | 0.121 | 0.110 | 0.134 | 0.126 | 0.157 | 0.120 | 0.134 | 0.137 | 0.098 | 0.064 | 0.120 |
| B | 0.153 | 0.126 | 0.114 | 0.116 | 0.156 | 0.172 | 0.117 | 0.133 | 0.137 | 0.086 | 0.131 | 0.142 |
| C | 0.115 | 0.150 | 0.111 | 0.121 | 0.106 | 0.102 | 0.115 | 0.114 | 0.118 | 0.090 | 0.104 | 0.135 |
| D | 0.114 | 0.130 | 0.124 | 0.092 | 0.087 | 0.109 | 0.133 | 0.099 | 0.112 | 0.122 | 0.117 | 0.132 |
| E | 0.114 | 0.124 | 0.110 | 0.127 | 0.093 | 0.108 | 0.108 | 0.104 | 0.107 | 0.111 | 0.134 | 0.155 |
| F | 0.122 | 0.127 | 0.117 | 0.122 | 0.145 | 0.129 | 0.121 | 0.109 | 0.104 | 0.152 | 0.105 | 0.143 |
| G | 0.121 | 0.118 | 0.127 | 0.127 | 0.119 | 0.124 | 0.104 | 0.120 | 0.121 | 0.109 | 0.133 | 0.119 |
| * H | 0.133 | 0.134 | 0.152 | (1.054) 4H4 | 0.127 | 0.110 | 0.133 | 0.112 | 0.126 | 0.092 | 0.127 | 0.099 |

Plate 5

|   | 1 | 2 | 3 | 4 | 5 | 6 | 7 | 8 | 9 | 10 | 11 | 12 |
|---|---|---|---|---|---|---|---|---|---|----|----|----|
| A | 0.101 | 0.109 | 0.144 | 1.005 | 0.031 | 0.039 | 0.037 | 0.047 | 0.043 | 0.038 | 0.042 | 0.048 |
| B | 0.111 | 0.129 | 0.109 | 0.997 | 0.025 | 0.032 | 0.043 | 0.038 | 0.037 | 0.039 | 0.040 | 0.042 |
| C | 0.119 | 0.121 | 0.093 | 0.979 | 0.024 | 0.040 | 0.038 | 0.037 | 0.042 | 0.040 | 0.052 | 0.046 |
| D | 0.116 | 0.102 | 0.125 | 0.035 | 0.027 | 0.035 | 0.040 | 0.038 | 0.042 | 0.038 | 0.040 | 0.044 |
| E | 0.120 | 0.092 | 0.101 | 0.986 | 0.027 | 0.032 | 0.036 | 0.035 | 0.041 | 0.037 | 0.038 | 0.038 |
| F | 0.105 | 0.116 | 0.110 | 0.748 | 0.025 | 0.037 | 0.044 | 0.036 | 0.035 | 0.037 | 0.044 | 0.050 |
| G | 0.122 | 0.108 | 0.114 | 0.961 | 0.022 | 0.040 | 0.041 | 0.041 | 0.041 | 0.037 | 0.043 | 0.049 |
| H | 0.135 | 0.101 | 0.167 | 0.037 | 0.030 | 0.032 | 0.031 | 0.036 | 0.036 | 0.041 | 0.041 | 0.061 | ium

SEQUENCE LISTING

```
<160> NUMBER OF SEQ ID NOS: 20

<210> SEQ ID NO 1
<211> LENGTH: 39
<212> TYPE: DNA
<213> ORGANISM: Artificial Sequence
<220> FEATURE:
<223> OTHER INFORMATION: 5' PCR primer for HE4 coding region.Native
      secretory signal peptide included.HindIII site and
      Kozak consensus sequence upstream of ATG

<400> SEQUENCE: 1
gttgttaagc ttgccgccat gcctgcttgt cgcctaggc                          39

<210> SEQ ID NO 2
<211> LENGTH: 36
<212> TYPE: DNA
<213> ORGANISM: Artificial Sequence
<220> FEATURE:
<223> OTHER INFORMATION: 3' antisense PCR primer for HE4 coding region
      STOP codon deleted/substitute in-frame BamHI
      restriction site for cloning

<400> SEQUENCE: 2
gttgttggat ccgaaattgg gagtgacaca ggacac                             36

<210> SEQ ID NO 3
<211> LENGTH: 390
<212> TYPE: DNA
<213> ORGANISM: Homo sapiens

<400> SEQUENCE: 3
```

```
aagcttgccg ccatgcctgc ttgtcgccta ggcccgctag ccgccgccct cctcctcagc    60
ctgctgctgt tcggcttcac cctagtctca ggcacaggag cagagaagac tggcgtgtgc   120
cccgagctcc aggctgacca gaactgcacg caagagtgcg tctcggacag cgaatgcgcc   180
gacaacctca agtgctgcag cgcgggctgt gccaccttct gctctctgcc caatgataag   240
gagggttcct gccccaggt gaacattaac tttccccagc tcggcctctg tcgggaccag   300
tgccaggtgg acagccagtg tcctggccag atgaaatgct gccgcaatgg ctgtgggaag   360
gtgtcctgtg tcactcccaa tttcggatcc                                   390
```

<210> SEQ ID NO 4
<211> LENGTH: 1077
<212> TYPE: DNA
<213> ORGANISM: Homo sapiens

<400> SEQUENCE: 4

```
atgcctgctt gtcgcctagg cccgctagcc gccgccctcc tcctcagcct gctgctgttc    60
ggcttcaccc tagtctcagg cacaggagca gagaagactg gcgtgtgccc cgagctccag   120
gctgaccaga actgcacgca agagtgcgtc tcggacagcg aatgcgccga caacctcaag   180
tgctgcagcg cgggctgtgc caccttctgc tctctgccca atgataagga gggttcctgc   240
ccccaggtga acattaactt tccccagctc ggcctctgtc gggaccagtg ccaggtggac   300
agccagtgtc ctggccagat gaaatgctgc cgcaatggct gtgggaaggt gtcctgtgtc   360
actcccaatt tcggatccga gcccaaatct tgtgacaaaa ctcacacatg cccaccgtgc   420
ccagcacctg aactcctggg gggaccgtca gtcttcctct tccccccaaa acccaaggac   480
accctcatga tctcccggac ccctgaggtc acatgcgtgg tggtggacgt gagccacgaa   540
gaccctgagg tcaagttcaa ctggtacgtg gacggcgtgg aggtgcataa tgccaagaca   600
aagccgcggg aggagcagta acagcacg taccgtgtgg tcagcgtcct caccgtcctg   660
caccaggact ggctgaatgg caaggagtac aagtgcaagg tctccaacaa agccctccca   720
gcccccatcg agaaaacaat ctccaaagcc aagggcagc cccgagaacc acaggtgtac   780
accctgcccc catcccggga tgagctgacc aagaaccagg tcagcctgac ctgcctggtc   840
aaaggcttct atcccagcga catcgccgtg gagtgggaga gcaatgggca gccggagaac   900
aactacaaga ccacgcctcc cgtgctggac tccgacggct ccttcttcct ctacagcaag   960
ctcaccgtgg acaagagcag gtggcagcag gggaacgtct tctcatgctc cgtgatgcat  1020
gaggctctgc acaaccacta cacgcagaag agcctctccc tgtctccggg taaatga     1077
```

<210> SEQ ID NO 5
<211> LENGTH: 358
<212> TYPE: PRT
<213> ORGANISM: Homo sapiens

<400> SEQUENCE: 5

```
Met Pro Ala Cys Arg Leu Gly Pro Leu Ala Ala Ala Leu Leu Leu Ser
 1               5                  10                  15

Leu Leu Leu Phe Gly Phe Thr Leu Val Ser Gly Thr Gly Ala Glu Lys
                20                  25                  30

Thr Gly Val Cys Pro Glu Leu Gln Ala Asp Gln Asn Cys Thr Gln Glu
            35                  40                  45

Cys Val Ser Asp Ser Glu Cys Ala Asp Asn Leu Lys Cys Cys Ser Ala
        50                  55                  60

Gly Cys Ala Thr Phe Cys Ser Leu Pro Asn Asp Lys Glu Gly Ser Cys
```

```
                65                  70                  75                  80
            Pro Gln Val Asn Ile Asn Phe Pro Gln Leu Gly Leu Cys Arg Asp Gln
                            85                  90                  95

Cys Gln Val Asp Ser Gln Cys Pro Gly Gln Met Lys Cys Cys Arg Asn
                        100                 105                 110

Gly Cys Gly Lys Val Ser Cys Val Thr Pro Asn Phe Gly Ser Glu Pro
                        115                 120                 125

Lys Ser Cys Asp Lys Thr His Thr Cys Pro Pro Cys Pro Ala Pro Glu
                    130                 135                 140

Leu Leu Gly Gly Pro Ser Val Phe Leu Phe Pro Pro Lys Pro Lys Asp
            145                 150                 155                 160

Thr Leu Met Ile Ser Arg Thr Pro Glu Val Thr Cys Val Val Val Asp
                            165                 170                 175

Val Ser His Glu Asp Pro Glu Val Lys Phe Asn Trp Tyr Val Asp Gly
                        180                 185                 190

Val Glu Val His Asn Ala Lys Thr Lys Pro Arg Glu Glu Gln Tyr Asn
                        195                 200                 205

Ser Thr Tyr Arg Val Val Ser Val Leu Thr Val Leu His Gln Asp Trp
                    210                 215                 220

Leu Asn Gly Lys Glu Tyr Lys Cys Lys Val Ser Asn Lys Ala Leu Pro
            225                 230                 235                 240

Ala Pro Ile Glu Lys Thr Ile Ser Lys Ala Lys Gly Gln Pro Arg Glu
                            245                 250                 255

Pro Gln Val Tyr Thr Leu Pro Pro Ser Arg Asp Glu Leu Thr Lys Asn
                        260                 265                 270

Gln Val Ser Leu Thr Cys Leu Val Lys Gly Phe Tyr Pro Ser Asp Ile
                        275                 280                 285

Ala Val Glu Trp Glu Ser Asn Gly Gln Pro Glu Asn Asn Tyr Lys Thr
                    290                 295                 300

Thr Pro Pro Val Leu Asp Ser Asp Gly Ser Phe Phe Leu Tyr Ser Lys
            305                 310                 315                 320

Leu Thr Val Asp Lys Ser Arg Trp Gln Gln Gly Asn Val Phe Ser Cys
                            325                 330                 335

Ser Val Met His Glu Ala Leu His Asn His Tyr Thr Gln Lys Ser Leu
                        340                 345                 350

Ser Leu Ser Pro Gly Lys
                    355

<210> SEQ ID NO 6
<211> LENGTH: 1098
<212> TYPE: DNA
<213> ORGANISM: Artificial Sequence
<220> FEATURE:
<223> OTHER INFORMATION: Human-Mouse synthetic fusion gene

<400> SEQUENCE: 6
aagcttgccg ccatgcctgc ttgtcgccta ggcccgctag ccgccgccct cctcctcagc      60
ctgctgctgt tcggcttcac cctagtctca ggcacaggag cagagaagac tggcgtgtgc     120
cccgagctcc aggctgacca gaactgcacg caagagtgcg tctcggacag cgaatgcgcc     180
gacaacctca gtgctgcagc gcgggctgt gccaccttct gctctctgcc aatgataag       240 gagggttcct gcccccaggt gaacattaac tttccccagc tcggcctctg tcgggaccag     300
tgccaggtgg acagccagtg tcctggccag atgaaatgct gccgcaatgg ctgtgggaag     360
gtgtcctgtg tcactcccaa tttcggatcc gagcccagag ggcccacaat caagccctgt     420
```

```
cctccatgca aatgcccagc accgaattca gctggtacct catccgtctt catcttccct    480
ccaaagatca aggatgtact catgatctcc ctgagcccca tagtcacatg tgtggtggtg    540
gatgtgagcg aggatgaccc agatgtccag atcagctggt ttgtgaacaa cgtggaagta    600
cacacagctc agacacaaac ccatagagag gattacaaca gtactctccg ggtggtcagt    660
gccctcccca tccagcacca ggactggatg agtggcaagg agttcaaatg caaggtcaac    720
aacaaagacc tcccagcgcc catcgagaga accatctcaa aacccaaagg gtcagtaaga    780
gctccacagg tatatgtctt gcctccacca gaagaagaga tgactaagaa acaggtcact    840
ctgacctgca tggtcacaga cttcatgcct gaagacattt acgtggagtg gaccaacaac    900
gggaaaacag agctaaacta caagaacact gaaccagtcc tggactctga tggttcttac    960
ttcatgtaca gcaagctgag agtggaaaag aagaactggg tggaaagaaa tagctactcc   1020
tgttcagtgg tccacgaggg tctgcacaat caccacacga ctaagagctt ctcccggact   1080
ccgggtaaat gatctaga                                                 1098
```

<210> SEQ ID NO 7
<211> LENGTH: 359
<212> TYPE: PRT
<213> ORGANISM: Artificial Sequence
<220> FEATURE:
<223> OTHER INFORMATION: Human-Mouse fusion protein

<400> SEQUENCE: 7

```
Met Pro Ala Cys Arg Leu Gly Pro Leu Ala Ala Leu Leu Leu Leu Ser
 1               5                  10                  15

Leu Leu Leu Phe Gly Phe Thr Leu Val Ser Gly Thr Gly Ala Glu Lys
                20                  25                  30

Thr Gly Val Cys Pro Glu Leu Gln Ala Asp Gln Asn Cys Thr Gln Glu
            35                  40                  45

Cys Val Ser Asp Ser Glu Cys Ala Asp Asn Leu Lys Cys Cys Ser Ala
        50                  55                  60

Gly Cys Ala Thr Phe Cys Ser Leu Pro Asn Asp Lys Glu Gly Ser Cys
 65                  70                  75                  80

Pro Gln Val Asn Ile Asn Phe Pro Gln Leu Gly Leu Cys Arg Asp Gln
                 85                  90                  95

Cys Gln Val Asp Ser Gln Cys Pro Gly Gln Met Lys Cys Cys Arg Asn
            100                 105                 110

Gly Cys Gly Lys Val Ser Cys Val Thr Pro Asn Phe Gly Ser Glu Pro
        115                 120                 125

Arg Gly Pro Thr Ile Lys Pro Cys Pro Cys Lys Cys Pro Ala Pro
    130                 135                 140

Asn Ser Ala Gly Thr Ser Ser Val Phe Ile Phe Pro Pro Lys Ile Lys
145                 150                 155                 160

Asp Val Leu Met Ile Ser Leu Ser Pro Ile Val Thr Cys Val Val Val
                165                 170                 175

Asp Val Ser Glu Asp Asp Pro Asp Val Gln Ile Ser Trp Phe Val Asn
            180                 185                 190

Asn Val Glu Val His Thr Ala Gln Thr Gln Thr His Arg Glu Asp Tyr
        195                 200                 205

Asn Ser Thr Leu Arg Val Val Ser Ala Leu Pro Ile Gln His Gln Asp
    210                 215                 220

Trp Met Ser Gly Lys Glu Phe Lys Cys Lys Val Asn Asn Lys Asp Leu
225                 230                 235                 240
```

```
Pro Ala Pro Ile Glu Arg Thr Ile Ser Lys Pro Lys Gly Ser Val Arg
                245                 250                 255
Ala Pro Gln Val Tyr Val Leu Pro Pro Glu Glu Met Thr Lys
            260                 265                 270
Lys Gln Val Thr Leu Thr Cys Met Val Thr Asp Phe Met Pro Glu Asp
            275                 280                 285
Ile Tyr Val Glu Trp Thr Asn Asn Gly Lys Thr Glu Leu Asn Tyr Lys
        290                 295                 300
Asn Thr Glu Pro Val Leu Asp Ser Asp Gly Ser Tyr Phe Met Tyr Ser
305                 310                 315                 320
Lys Leu Arg Val Glu Lys Lys Asn Trp Val Glu Arg Asn Ser Tyr Ser
                325                 330                 335
Cys Ser Val Val His Glu Gly Leu His Asn His His Thr Thr Lys Ser
                340                 345                 350
Phe Ser Arg Thr Pro Gly Lys
            355

<210> SEQ ID NO 8
<211> LENGTH: 583
<212> TYPE: DNA
<213> ORGANISM: Homo sapiens

<400> SEQUENCE: 8
cccctgcacc ccgcccggca tagcaccatg cctgcttgtc gcctaggccc gctagccgcc      60
gccctcctcc tcagcctgct gctgttcggc ttcaccctag tctcaggcac aggagcagag     120
aagactggcg tgtgccccga gctccaggct gaccagaact gcacgcaaga gtgcgtctcg     180
gacagcgaat gcgccgacaa cctcaagtgc tgcagcgcgg gctgtgccac cttctgcctt     240
ctctgcccca atgataagga gggttcctgc cccaggtgaa cattaacttt ccccagctc     300
ggcctctgtc gggaccagtg ccaggtggac acgcagtgtc ctggccagat gaaatgctgc     360
cgcaatggct gtgggaaggt gtcctgtgtc actcccaatt ctgaggtcc agccaccacc      420
aggctgagca gtgaggagag aaagtttctg cctggccctg catctggttc cagcccacct    480
gccctcccct ttttcgggac tctgtattcc ctcttggggt gaccacagct tctccctttc    540
ccaaccaata aagtaaccac tttcagcaaa aaaaaaaaa aaa                       583

<210> SEQ ID NO 9
<211> LENGTH: 125
<212> TYPE: PRT
<213> ORGANISM: Homo sapiens

<400> SEQUENCE: 9

Met Pro Ala Cys Arg Leu Gly Pro Leu Ala Ala Ala Leu Leu Leu Ser
1               5                  10                  15
Leu Leu Leu Phe Gly Phe Thr Leu Val Ser Gly Thr Gly Ala Glu Lys
            20                  25                  30
Thr Gly Val Cys Pro Glu Leu Gln Ala Asp Gln Asn Cys Thr Gln Glu
        35                  40                  45
Cys Val Ser Asp Ser Glu Cys Ala Asp Asn Leu Lys Cys Cys Ser Ala
    50                  55                  60
Gly Cys Ala Thr Phe Cys Leu Leu Cys Pro Asn Asp Lys Glu Gly Ser
65                  70                  75                  80
Cys Pro Gln Val Asn Ile Asn Phe Pro Gln Leu Gly Leu Cys Arg Asp
                85                  90                  95
```

Gln Cys Gln Val Asp Thr Gln Cys Pro Gly Gln Met Lys Cys Cys Arg
                100                 105                 110

Asn Gly Cys Gly Lys Val Ser Cys Val Thr Pro Asn Phe
            115                 120                 125

<210> SEQ ID NO 10
<211> LENGTH: 486
<212> TYPE: DNA
<213> ORGANISM: Homo sapiens

<400> SEQUENCE: 10
tgagagaaag cggccgcacc ccgcccggca tagcaccatg cctgcttgtc gcctaggccc     60
gctagccgcc gccctcctcc tcagcctgct gctgttcggc ttcaccctag tctcaggcac    120
aggagcagag aagactggcg tgtgccccga gctccaggct gaccagaact gcacgcaaga    180
gtgcgtctcg gacagcgaat gcgccgacaa cctcaagtgc tgcagcgcgg gctgtgccac    240
cttctgctct ctgcccaatg ataaggaggg ttcctgcccc caggtgaaca ttaactttcc    300
ccagctcggc ctctgtcggg accagtgcca ggtggacagc cagtgtcctg gccagatgaa    360
atgctgccgc aatggctgtg gaaggtgtc ctgtgtcact cccaatttct gagctccggc    420
caccaccagg ctgagcagtg aagatagaaa gtttctgcct ggccctgcag cgtgttacag    480
cccacc                                                                486

<210> SEQ ID NO 11
<211> LENGTH: 124
<212> TYPE: PRT
<213> ORGANISM: Homo sapiens

<400> SEQUENCE: 11

Met Pro Ala Cys Arg Leu Gly Pro Leu Ala Ala Leu Leu Leu Ser
  1               5                  10                  15

Leu Leu Leu Phe Gly Phe Thr Leu Val Ser Gly Thr Gly Ala Glu Lys
                20                  25                  30

Thr Gly Val Cys Pro Glu Leu Gln Ala Asp Gln Asn Cys Thr Gln Glu
            35                  40                  45

Cys Val Ser Asp Ser Glu Cys Ala Asp Asn Leu Lys Cys Cys Ser Ala
        50                  55                  60

Gly Cys Ala Thr Phe Cys Ser Leu Pro Asn Asp Lys Glu Gly Ser Cys
 65                  70                  75                  80

Pro Gln Val Asn Ile Asn Phe Pro Gln Leu Gly Leu Cys Arg Asp Gln
                85                  90                  95

Cys Gln Val Asp Ser Gln Cys Pro Gly Gln Met Lys Cys Cys Arg Asn
                100                 105                 110

Gly Cys Gly Lys Val Ser Cys Val Thr Pro Asn Phe
            115                 120

<210> SEQ ID NO 12
<211> LENGTH: 374
<212> TYPE: DNA
<213> ORGANISM: Homo sapiens

<400> SEQUENCE: 12
ccatgcctgc ttgtcgccta ggcccgctag ccgccgccct cctcctcagc ctgctgctgt     60
tcggcttcac cctagtctca ggcacaggag cagagaagac tggcgtgtgc cccgagctcc    120
aggctgacca gaactgcacg caagagtgcg tctcggacag cgaatgcgcc gacaacctca    180
agtgctgcag cgcgggctgt gccaccttct gctctctgcc caatgataag gagggttcct    240

```
gcccccaggt gaacattaac tttcccagc tcggcctctg tcgggaccag tgccaggtgg        300
acagccagtg tcctggccag atgaaatgct gccgcaatgg ctgtgggaag gtgtcctgtg        360
tcactcccaa tttc                                                          374
```

```
<210> SEQ ID NO 13
<211> LENGTH: 124
<212> TYPE: PRT
<213> ORGANISM: Homo sapiens

<400> SEQUENCE: 13
```

Met Pro Ala Cys Arg Leu Gly Pro Leu Ala Ala Leu Leu Leu Ser
 1               5                  10                  15

Leu Leu Leu Phe Gly Phe Thr Leu Val Ser Gly Thr Gly Ala Glu Lys
            20                  25                  30

Thr Gly Val Cys Pro Glu Leu Gln Ala Asp Gln Asn Cys Thr Gln Glu
        35                  40                  45

Cys Val Ser Asp Ser Glu Cys Ala Asp Asn Leu Lys Cys Cys Ser Ala
    50                  55                  60

Gly Cys Ala Thr Phe Cys Ser Leu Pro Asn Asp Lys Glu Gly Ser Cys
65                  70                  75                  80

Pro Gln Val Asn Ile Asn Phe Pro Gln Leu Gly Leu Cys Arg Asp Gln
                85                  90                  95

Cys Gln Val Asp Ser Gln Cys Pro Gly Gln Met Lys Cys Cys Arg Asn
            100                 105                 110

Gly Cys Gly Lys Val Ser Cys Val Thr Pro Asn Phe
        115                 120

```
<210> SEQ ID NO 14
<211> LENGTH: 19
<212> TYPE: PRT
<213> ORGANISM: Homo sapiens

<400> SEQUENCE: 14
```

Glu Val Glu Lys Thr Ala Cys Pro Ser Gly Lys Lys Ala Arg Glu Ile
 1               5                  10                  15

Asp Glu Ser

```
<210> SEQ ID NO 15
<211> LENGTH: 20
<212> TYPE: DNA
<213> ORGANISM: Artificial Sequence
<220> FEATURE:
<223> OTHER INFORMATION: Forward HE4 real-time PCR primer

<400> SEQUENCE: 15
agcagagaag actggcgtgt                                                     20

<210> SEQ ID NO 16
<211> LENGTH: 21
<212> TYPE: DNA
<213> ORGANISM: Artificial Sequence
<220> FEATURE:
<223> OTHER INFORMATION: Reverse HE4 real-time PCR primer

<400> SEQUENCE: 16
gaaagggaga agctgtggtc a                                                   21

<210> SEQ ID NO 17
<211> LENGTH: 20
```

```
<212> TYPE: DNA
<213> ORGANISM: Artificial Sequence
<220> FEATURE:
<223> OTHER INFORMATION: Forward primer

<400> SEQUENCE: 17
cgacgcttct tcaaggccaa                                               20

<210> SEQ ID NO 18
<211> LENGTH: 20
<212> TYPE: DNA
<213> ORGANISM: Artificial Sequence
<220> FEATURE:
<223> OTHER INFORMATION: Reverse primer

<400> SEQUENCE: 18
atggaagccc aagctgctga                                               20

<210> SEQ ID NO 19
<211> LENGTH: 36
<212> TYPE: DNA
<213> ORGANISM: Artificial Sequence
<220> FEATURE:
<223> OTHER INFORMATION: Forward sense primer

<400> SEQUENCE: 19
gttgtcggat ccgagcccag agggcccaca atcaag                             36

<210> SEQ ID NO 20
<211> LENGTH: 43
<212> TYPE: DNA
<213> ORGANISM: Artificial Sequence
<220> FEATURE:
<223> OTHER INFORMATION: Reverse anti- sense primer

<400> SEQUENCE: 20
gttgtttcta gattatcatt tacccggagt ccgggagaag ctc                     43
```

DIAGNOSIS OF OVARIAN CARCINOMAS

CROSS-REFERENCE TO RELATED APPLICATION

This application claims the benefit of U.S. Provisional Patent Application No. 60/316,537 filed Aug. 29, 2001, which is incorporated herein by reference in its entirety.

STATEMENT OF POTENTIAL GOVERNMENT RIGHTS IN THE INVENTION

Part of the invention was made in the course of research sponsored by NIH Grant No. R01CA85780 (National Cancer Institute). The United States Government may have certain rights in this invention.

TECHNICAL FIELD

The present invention relates generally to malignant conditions such as cancer, and in particular to methods and compositions for diagnosing certain carcinomas such as ovarian carcinoma.

BACKGROUND OF THE INVENTION

Cancer includes a broad range of diseases, affecting approximately one in four individuals worldwide. The severity of the adverse impact of cancer is profound, influencing medical policy and procedure as well as society generally. Because a hallmark of many types of cancer is rapid and unregulated proliferation of malignant cells, an overarching problem in improving approaches to cancer is the need for early detection and diagnosis. Numerous attempts have been made to develop accurate and reliable criteria for diagnosing the presence of a malignant condition. In particular, efforts have been directed to the use of serologically defined antigenic markers known as tumor associated antigens, which are either uniquely expressed by cancer cells or are present at markedly higher levels in subjects having a malignant condition.

However, due to the high heterogeneity of tumor associated antigen expression, for example the extreme diversity of carcinoma antigens, there is a need for additional tumor markers that are useful in cancer diagnosis. Many monoclonal antibodies reactive with carcinoma associated antigens are known (see, e.g., Papsidero, 1985 *Semin. Surg. Oncol.* 1:171, Allum et al., 1986 *Surg. Ann.* 18:41). These and other described monoclonal antibodies bind to a variety of different carcinoma associated antigens including glycoproteins, glycolipids and mucins (see, e.g., Fink et al., 1984 *Prog. Clin. Pathol.* 9:121; U.S. Pat. No. 4,737,579; U.S. Pat. No. 4,753,894; U.S. Pat. No. 4,579,827; U.S. Pat. No. 4,713,352). Many such monoclonal antibodies recognize tumor associated antigens that exhibit restricted expression on some but not other tumors originating in a given cell lineage or tissue type.

There are only relatively few examples of tumor associated antigens that appear to be useful for identifying a particular type of malignancy. Monoclonal antibody B72.3, for example, specifically binds to a high molecular mass (>$10^6$ Da) tumor-associated mucin antigen that is selectively expressed on a number of different carcinomas, including most if not all ovarian carcinomas and an overwhelming majority of non-small cell lung carcinomas, colon carcinomas and breast carcinomas (see, e.g., Johnston, 1987 *Acta Cytol.* 1:537; U.S. Pat. No. 4,612,282). Nevertheless, detection of cell-associated tumor markers such as the mucin antigen recognized by B72.3 following surgical resection of a tumor may be of limited usefulness for diagnostic screening, in which early detection of a malignant condition prior to accumulation of substantial tumor mass is preferred.

An alternative to the diagnosis of a particular type of cancer by screening surgically resected specimens for tumor associated antigens, where invasive surgery is usually indicated only after detection of an accumulated tumor mass, would be to provide compositions and methods for detecting such antigens in samples obtained from subjects by non-invasive or minimally invasive procedures. In ovarian and other carcinomas, for example, there are currently a number of soluble tumor associated antigens that are detectable in samples of readily obtained biological fluids such as serum or mucosal secretions. One such marker is CA125, a carcinoma associated antigen that is also shed into the bloodstream, where it is detectable in serum (e.g., Bast et al., 1983 *N. Eng. J. Med.* 309:883; Lloyd et al., 1997 *Int. J. Canc.* 71:842). CA125 levels in serum and other biological fluids have been measured along with levels of other markers, for example, carcinoembryonic antigen (CEA), squamous cell carcinoma antigen (SCC), tissue polypeptide specific antigen (TPS), sialyl TN mucin (STN) and placental alkaline phosphatase (PLAP), in efforts to provide diagnostic and/or prognostic profiles of ovarian and other carcinomas (e.g., Sarandakou et al., 1997 *Acta Oncol.* 36:755; Sarandakou et al., 1998 *Eur. J. Gynaecol. Oncol.* 19:73; Meier et al., 1997 *Anticanc. Res.* 17(4B):2945; Kudoh et al., 1999 *Gynecol. Obstet. Invest.* 47:52; Ind et al., 1997 *Br. J. Obstet. Gynaecol.* 104:1024; Bell et al. 1998 *Br. J. Obstet. Gynaecol.* 105:1136; Cioffi et al., 1997 *Tumori* 83:594; Meier et al. 1997 *Anticanc. Res.* 17(4B):2949; Meier et al., 1997 *Anticanc. Res.* 17(4B):3019).

Elevated levels of serum CA125 alone or in combination with other known indicators, however, do not provide a definitive diagnosis of malignancy, or of a particular malignancy such as ovarian carcinoma. For example, elevated CA125, CEA and SCC in vaginal fluid and serum correlate most strongly with inflammation in benign gynecological diseases, relative to cervical cancer and genital tract cancers (e.g., Moore et al., 1998 *Infect. Dis. Obstet. Gynecol.* 6:182; Sarandakou et al., 1997 *Acta Oncol.* 36:755). As another example, elevated serum CA125 may also accompany neuroblastoma (e.g., Hirokawa et al., 1998 *Surg. Today* 28:349), while elevated CEA and SCC, among others, may accompany colorectal cancer (Gebauer et al., 1997 *Anticanc. Res.* 17(4B):2939). Another marker, the differentiation antigen mesothelin, is expressed on the surfaces of normal mesothelial cells and also on certain cancer cells, including epithelial ovarian tumors and mesotheliomas. Compositions and methods pertaining to mesothelin (Chang et al., 1992 *Canc. Res.* 52:181; Chang et al., 1992 *Int. J. Canc.* 50:373; Chang et al., 1992 *Int. J. Canc.* 51:548; Chang et al., 1996 *Proc. Nat. Acad. Sci. USA* 93:136; Chowdhury et al., 1998 *Proc. Nat. Acad. Sci. USA* 95:669; Yamaguchi et al., 1994 *J. Biol. Chem.* 269:805; Kojima et al., 1995 *J. Biol. Chem.* 270:21984) and structurally related mesothelin related antigen (MRA; see, e.g., Scholler et al., 1999 *Proc. Nat. Acad. Sci. USA* 96:11531) are known in the art, including uses in cancer detection and therapies as described in WO 00/50900 and in U.S. application Ser. No. 09/513,597. Thus the compelling need for additional markers to be used, including markers useful in multi-factor diagnostic screening, is apparent. (See, e.g., Sarandakou et al., 1998; Kudoh et al., 1999; Ind et al., 1997.)

As described in greater detail below, such additional markers might be usefully provided from within the "four-disulfide core" family of proteins, which comprises a heterogeneous group of small acid- and heat-stable molecules of divergent function and which includes human epididymal four-disulfide core protein, or "HE4" (Kirchhoff et al., 1991 *Biol. Reprod.* 45:350-357; Wang et al., 1999 *Gene* 229:101; Schummer et al., 1999 *Gene* 238:375). The conserved spacing of eight core cysteine residues in the amino acid sequences of four-disulfide core family member polypeptides is thought to direct the folding of these molecules into a compact and stable structure. Many of the members of the four-disulfide core family are protease inhibitors; however, for some family members, including HE4, no function has yet been definitively identified. Other members of the four-disulfide core family of proteins include Wp-protein, SLP-1, and ps20, and additional members of the four-disulfide core family of proteins have been isolated from several species. These proteins share several properties, including their small size and their heat- and acid-stable structure, which is stabilized by the four-disulfide core. These proteins are made by secretory cells, and are found in mucous secretions such as seminal plasma, milk, parotid, and cervical secretions.

The prototype molecule of the four-disulfide core family, Wp-protein, is also known as the whey phosphoprotein, and has been cloned (Dandekar et al., 1982 *Proc. Natl. Acad. Sci. USA* 79: 3987-3991). Whey phosphoprotein is expressed in milk at approximately 1-2 mg/ml, but is not expressed by breast carcinomas, where the gene is hypermethylated. No inhibitory activity towards proteases has been found for whey phosphoprotein. However, overexpression of the gene in transgenic animals impairs development of mammary alveolar cells (Burdon et al, 1991 *Mechanisms Dev.* 36: 67-74), suggesting an important role for this protein during lactation. The secretory leukocyte protease inhibitor (SLP-1), another four-disulfide core family protein, was cloned from human cervix uteri, but is also present in other mucus secretions including seminal plasma and parotid secretions (Heinzel et al, 1986 *Eur. J. Biochem.* 160: 61-67). SLP-1 is a two domain protein of 12 kDa that is a potent inhibitor of trypsin, chymotrypsin, elastase, and cathepsin G. The crystal structure of SLP-1 complexed with chymotrypsin has been published (Grutter et al, 1988 *EMBO J.* 7: 345-351). These data showed that SLP-1 domains can work independently and simultaneously to inhibit different proteases, and identified a small (8 amino acids) active site in domain two that binds to chymotrypsin.

Elafin is a single domain protein member of the four-disulfide core family that was isolated from human psoriatic skin to determine the amino acid sequence of this polypeptide (Wiedow et al, 1990 *J. Biol. Chem.* 265: 14791-14795). Elafin is a potent inhibitor of elastase, but does not exhibit apparent inhibitory activity toward other proteases such as trypsin, chymotrypsin, cathepsin G or plasmin. The amino acid sequence of elafin shows 38% homology with the C-terminal region (domain 1) of SLP-1. The gene encoding the ps20 protein was recently isolated from smooth muscle, and the ps20 protein was expressed by transfection of the gene into mammalian cells (Larsen et al, 1998 *J. Biol. Chem.* 273: 4574-4584). ps20 was found to inhibit growth of carcinoma cells, and ps20 has been referred to as a growth inhibitor; however, no direct functional activity such as inhibition of proteases has been described so far for this protein.

As noted above, no protease inhibitory activity has been identified for HE4, which was initially identified in epididymal epithelial cells, although other small acid and heat stable proteinase inhibitors have been characterized from seminal plasma, and are thought to play a role in fertility by binding to spermatozoa and regulating the interaction of spermatozoa with the extracellular matrices of the egg (Fitz et al., in *Proteases and Biological Controls*, Reich, E., Rifkin, D., Shaw, E. (eds.), 1975 Cold Spring Harbor Laboratory Press, Cold Spring Harbor, N.Y., pp. 737-766; Saling, 1989 *Oxf. Rev. Reprod. Biol.* 11: 339-388). HE4 cDNA was first isolated from human epididymis (Kirchhoff et al., 1991 *Biol. Reprod.* 45:350-357), and HE4 cDNA was later detected with high frequency in cDNA libraries constructed from ovarian carcinomas (Wang et al., 1999 *Gene* 229:101; Schummer et al., 1999 *Gene* 238:375).

For reasons given above, clearly there is a need for improved diagnostic markers and therapeutic targets for the detection and treatment of malignant conditions, such as carcinomas. The compositions and methods of the present invention overcome these limitations of the prior art by providing a method of screening for the presence of a malignant condition using antibodies specific for HE4 and/or HE4-related antigens to detect polypeptides that naturally occur in soluble form and/or on cell surfaces, and offer other related advantages.

SUMMARY OF THE INVENTION

The present invention is directed to compositions and methods useful in screening for the presence of a malignant condition in a subject. In particular, the invention relates to the unexpected finding that soluble and cell surface forms of HE4 polypeptides referred to herein as HE4a, or HE4a molecules naturally occurring in soluble form and having an antigenic determinant reactive with at least one antibody that is specific for an HE4a polypeptide, can be detected in a biological sample from a subject.

It is one aspect of the invention to provide a method of screening for the presence of a malignant condition in a subject comprising contacting a biological sample from a subject with at least one antibody specific for a HE4a antigen polypeptide to determine the presence in the biological sample of a molecule naturally occurring in soluble form in the sample, or occurring as a cell surface molecule in certain embodiments wherein the sample comprises at least one cell from the subject, the molecule having an antigenic determinant that is reactive with the at least one antibody, under conditions and for a time sufficient to detect binding of the antibody to the antigenic determinant, and therefrom detecting the presence of a malignant condition. In some embodiments the biological sample is blood, serum, serosal fluid, plasma, lymph, urine, cerebrospinal fluid, saliva, a mucosal secretion, a vaginal secretion, ascites fluid, pleural fluid, pericardial fluid, peritoneal fluid, abdominal fluid, culture medium, conditioned culture medium or lavage fluid.

In certain other embodiments, the HE4a antigen polypeptide comprises a polypeptide having the amino acid sequence set forth in any one of SEQ ID NOS:5, 7, 9 or 11, or a fragment or derivative thereof. In another embodiment the HE4a antigen polypeptide variant is a splice variant. In certain embodiments of the invention, the antibody comprises a polyclonal antibody, and in other embodiments the antibody comprises an affinity purified antibody. In particularly preferred embodiments the antibody comprises a monoclonal antibody. In another embodiment the antibody comprises a recombinant antibody and in another embodiment the antibody comprises a chimeric antibody. In another embodiment, the antibody comprises a humanized antibody. In another embodiment, the antibody comprises a single chain antibody.

In some embodiments of the invention, detection of binding of the antibody to an antigenic determinant comprises detection of a radionuclide. In other embodiments, detection of binding of the antibody to an antigenic determinant comprises detection of a fluorophore. In another embodiment, detection of binding of the antibody to an antigenic determinant comprises detection of a binding event between an avidin molecule and a biotin molecule and in another embodiment detection of binding of the antibody to an antigenic determinant comprises detection of a binding event between a streptavidin molecule and a biotin molecule. In certain embodiments detection of binding of the antibody to an antigenic determinant comprises spectrophotometric detection of a product of an enzyme reaction. In some embodiments of the invention, the at least one antibody is detectably labeled, while in certain other embodiments the at least one antibody is not detectably labeled and detection of binding of the antibody to an antigenic determinant is indirect.

According to certain embodiments of the invention, the malignant condition may be adenocarcinoma, mesothelioma, ovarian carcinoma, pancreatic carcinoma or non-small cell lung carcinoma.

It is another aspect of the invention to provide a method of screening for the presence of a malignant condition in a subject comprising contacting a biological sample from a subject with at least one antibody to determine the presence in the biological sample of a molecule selected from the group consisting of (i) a molecule naturally occurring in soluble form in the sample, and (ii) a cell surface molecule wherein the sample comprises a cell from the subject, the molecule having an antigenic determinant that is reactive with the at least one antibody, the antigen combining site of which competitively inhibits the immunospecific binding of a monoclonal antibody that is 2H5, 3D8 or 4H4, under conditions and for a time sufficient to detect binding of the antibody to the antigenic determinant, and therefrom detecting the presence of a malignant condition.

Another aspect of the invention provides a method of screening for the presence of a malignant condition in a subject comprising contacting a biological sample from a subject with at least one antibody to determine the presence in the biological sample of a molecule selected from the group consisting of (i) a molecule naturally occurring in soluble form in the sample, and (ii) a cell surface molecule wherein the sample comprises a cell from the subject, the molecule having an antigenic determinant that is reactive with the antibody, the antigen combining site of which competitively inhibits the immunospecific binding of monoclonal antibody 3D8, under conditions and for a time sufficient to detect binding of the antibody to the antigenic determinant, and therefrom detecting the presence of a malignant condition.

Still another aspect of the invention provides a method of screening for the presence of a malignant condition in a subject comprising contacting a biological sample from a subject with at least one antibody specific for a HE4a antigen polypeptide to determine the presence in the biological sample of a molecule selected from the group consisting of (i) a molecule naturally occurring in soluble form in the sample, and (ii) a cell surface molecule wherein the sample comprises a cell from the subject, the molecule having an antigenic determinant that is reactive with the antibody, under conditions and for a time sufficient to detect binding of the at least one antibody to the antigenic determinant, wherein the at least one antibody immunospecifically binds to HE4a antigen, and therefrom detecting the presence of a malignant condition. In certain embodiments, the HE4a antigen is also immunospecifically reactive with monoclonal antibody 3D8, 2H5 or 4H4.

Turning to another aspect, the invention provides a method of screening for the presence of a malignant condition in a subject comprising contacting a biological sample from a subject with at least one antibody specific for a HE4a antigen polypeptide to determine the presence in the biological sample of a molecule selected from the group consisting of (i) a molecule naturally occurring in soluble form in the sample, and (ii) a cell surface molecule wherein the sample comprises a cell from the subject, the molecule having an antigenic determinant that is reactive with the at least one antibody, the antigen combining site of which competitively inhibits the immunospecific binding of a monoclonal antibody that is 2H5 or 4H4, under conditions and for a time sufficient to detect binding of the antibody to the antigenic determinant, wherein the at least one antibody immunospecifically binds to HE4a antigen, and therefrom detecting the presence of a malignant condition. In certain embodiments the mesothelin related antigen is also immunospecifically reactive with monoclonal antibody 3D8.

Turning to another aspect, the invention provides a method of screening for the presence of a malignant condition in a subject comprising contacting a biological sample from a subject with at least one immobilized first antibody specific for a HE4a antigen polypeptide to determine the presence in the biological sample of a molecule naturally occurring in soluble form in the sample, under conditions and for a time sufficient to specifically bind the at least one immobilized first antibody to the HE4a antigen polypeptide and thereby form an immune complex; removing constituents of the sample that do not specifically bind to the at least one immobilized first antibody; and contacting the immune complex with at least one second antibody specific for a HE4a antigen polypeptide, wherein the antigen combining site of the at least one second antibody does not competitively inhibit the antigen combining site of the at least one immobilized first antibody, under conditions and for a time sufficient to detect specific binding of the at least one second antibody to the HE4a antigen polypeptide, and therefrom detecting the presence of a malignant condition.

In yet another aspect the invention provides a method of screening for the presence of a malignant condition in a subject comprising contacting a biological sample from a subject with at least one immobilized first antibody specific for a HE4a antigen polypeptide to determine the presence in the biological sample of a molecule naturally occurring in soluble form in the sample, wherein the antigen combining site of the at least one first antibody competitively inhibits the immunospecific binding of monoclonal antibody 3D8 under conditions and for a time sufficient to specifically bind the at least one immobilized first antibody to the HE4a antigen polypeptide and thereby form an immune complex; removing constituents of the sample that do not specifically bind to the at least one immobilized first antibody; and contacting the immune complex with at least one second antibody specific for a HE4a antigen polypeptide, wherein the antigen combining site of the at least one second antibody does not competitively inhibit the immunospecific binding of monoclonal antibody 2H5, under conditions and for a time sufficient to detect specific binding of the at least one second antibody to the HE4a antigen polypeptide, and therefrom detecting the presence of a malignant condition.

In another aspect, the invention provides a method of screening for the presence of a malignant condition in a subject comprising contacting a biological sample from a subject with at least one immobilized first antibody specific for a HE4a antigen polypeptide to determine the presence in the biological sample of a molecule naturally occurring in soluble form in the sample, wherein the antigen combining site of the at least one first antibody competitively inhibits the immunospecific binding of monoclonal antibody 3D8 under conditions and for a time sufficient to specifically bind the at least one immobilized first antibody to the HE4a antigen polypeptide and thereby form an immune complex; removing constituents of the sample that do not specifically bind to the at least one immobilized first antibody; and contacting the immune complex with at least one second antibody specific for a HE4a antigen polypeptide, wherein the antigen combining site of the at least one second antibody does not competitively inhibit the immunospecific binding of monoclonal antibody 4H4, under conditions and for a time sufficient to detect specific binding of the at least one second antibody to the mesothelin related antigen polypeptide, and therefrom detecting the presence of a malignant condition.

In certain embodiments the subject invention method further comprises determining the presence in the sample of at least one soluble marker of a malignant condition, wherein the marker is a mesothelin related antigen, carcinoembryonic antigen, CA125, sialyl TN, squamous cell carcinoma antigen, tissue polypeptide antigen, or placental alkaline phosphatase.

It is another aspect of the invention to provide a method of screening for the presence of a malignant condition in a subject comprising contacting each of (i) a first biological sample from a first subject suspected of having a malignant condition, and (ii) a second biological sample from a second subject known to be free of a malignant condition, with at least one antibody specific for a HE4a antigen polypeptide to determine the presence in each of the first and second biological samples of a molecule selected from the group consisting of (i) a molecule naturally occurring in soluble form in the sample, and (ii) a cell surface molecule wherein the first and second biological samples each comprise, respectively, a cell from the first and second subjects, the molecule having an antigenic determinant that is reactive with the at least one antibody, under conditions and for a time sufficient to detect binding of the antibody to the antigenic determinant, and comparing a level of detectable binding of the antibody to the antigenic determinant in the first biological sample to a level of detectable binding of the antibody to the antigenic determinant in the second biological sample, and therefrom detecting the presence of a malignant condition.

In another aspect, the invention provides a method of screening for the presence of a malignant condition in a subject comprising detecting in a biological sample from the subject the presence of an antibody that immunospecifically binds to a HE4a antigen polypeptide. In certain embodiments the mesothelin related antigen polypeptide comprises a polypeptide having the amino acid sequence set forth in any one of SEQ ID NOS:5, 7, 11 or 13.

Turning to another aspect, the invention provides an antibody specific for a HE4a antigen polypeptide, comprising a monoclonal immunoglobulin variable region that specifically binds to a HE4a antigen polypeptide comprising the amino acid sequence set forth in any one of SEQ ID NOS:5, 7, 11 or 13. In certain embodiments the antibody is a fusion protein, while in certain other embodiments the antibody is a single chain antibody. In certain other embodiments, the HE4a antigen polypeptide further comprises a glycosylated polypeptide. In another embodiment, the antibody specifically binds to a HE4a antigen polypeptide sequence set forth in SEQ ID NO:11 but does not specifically bind to a polypeptide sequence set forth in SEQ ID NO:9, or the antibody specifically binds to both the HE4a antigen polypeptide sequence set forth in SEQ ID NO:11 and to the polypeptide sequence set forth in SEQ ID NO:9. In certain embodiments the antibody is monoclonal antibody 2H5, 3D8 or 4H4.

In still another aspect, the invention provides a method of screening for the presence of a malignant condition in a subject comprising contacting a biological sample from a subject with a detectably labeled HE4a polypeptide, under conditions and for a time sufficient to detect binding to the HE4a polypeptide of an antibody naturally occurring in soluble form in the sample, and therefrom detecting the presence of a malignant condition.

Turning to another aspect, the invention provides an isolated nucleic acid molecule that is a nucleic acid molecule encoding a HE4a antigen polypeptide, the polypeptide comprising an amino acid sequence set forth in SEQ ID NOS:5, 7, 11 or 13; or that is a nucleic acid molecule that encodes a HE4a antigen polypeptide or fusion protein or that is capable of hybridizing to such a nucleic acid molecule encoding a HE4a antigen under moderately stringent conditions, wherein the isolated nucleic acid molecule is not a nucleic acid molecule consisting of the nucleotide sequence set forth in SEQ ID NO:9. In certain embodiments the invention provides an antisense oligonucleotide comprising at least 15 consecutive nucleotides complementary to the nucleic acid molecule encoding a HE4a antigen polypeptide.

In other embodiments, the present invention provides a fusion protein comprising a polypeptide sequence fused to a HE4a antigen polypeptide. In certain further embodiments, the fusion domain is an immunoglobulin or a variant or fragment thereof. In certain further embodiments, the polypeptide sequence fused to a HE4a antigen polypeptide is cleavable by a protease. In another embodiment, the polypeptide sequence is an affinity tag polypeptide having affinity for a ligand.

In other embodiments, the invention provides a recombinant expression construct comprising at least one promoter operably linked to a nucleic acid molecule encoding a HE4a antigen polypeptide as described above. In certain embodiments the promoter is a regulated promoter and in certain other embodiments the HE4a antigen polypeptide is expressed as a fusion protein with a polypeptide product of a second nucleic acid sequence. In a further embodiment the polypeptide product of the second nucleic acid sequence is an immunoglobulin constant region. In another embodiment the expression construct is a recombinant viral expression construct. According to other embodiments, the invention provides a host cell comprising a recombinant expression construct as provided herein. In one embodiment the host cell is a prokaryotic cell and in another embodiment the host cell is a eukaryotic cell.

In another aspect, the invention provides a method of producing a recombinant HE4a antigen polypeptide by culturing a host cell comprising a recombinant expression construct comprising at least one promoter operably linked to a nucleic acid molecule encoding a HE4a antigen polypeptide as provided herein. In certain embodiments the promoter is a regulated promoter. In another embodiment the invention provides a method of producing a recombinant HE4a antigen polypeptide, by culturing a host cell infected with the recombinant viral expression construct as provided herein for expression of recombinant HE4a antigen polypeptide.

The present invention also provides, in another embodiment, a method for detecting HE4a expression in a sample by contacting an antisense oligonucleotide as described above with a sample comprising a nucleic acid sequence encoding a HE4a polypeptide having the amino acid sequence set forth in SEQ ID NO:11, or a fragment or variant thereof; and detecting in the sample an amount of HE4a polypeptide-encoding nucleic acid that hybridizes to the antisense oligonucleotide, and therefrom detecting HE4a expression in the sample. In another embodiment the amount of HE4a polypeptide-encoding nucleic acid that hybridizes to the antisense oligonucleotide is determined using polymerase chain reaction. In another embodiment the amount of HE4a polypeptide-encoding nucleic acid that hybridizes to the antisense oligonucleotide is determined using a hybridization assay. In another embodiment the sample comprises an RNA or cDNA preparation.

According to certain other embodiments of the present invention, there is provided a method for treating a malignant condition, comprising administering to a patient in need thereof a composition comprising an antibody specific for a HE4a antigen polypeptide, the antibody comprising a monoclonal immunoglobulin variable region that specifically binds to a HE4a antigen polypeptide having an amino acid sequence set forth in SEQ ID NO:11. In another embodiment the invention provides a method for treating a malignant condition, comprising administering to a patient in need thereof a composition comprising a HE4a polypeptide having an amino acid sequence set forth in SEQ ID NO:11, or a fragment thereof. In certain further embodiments the composition induces production in the patient of an antibody that is capable of specifically binding to a HE4a polypeptide having an amino acid sequence set forth in SEQ ID NO:11, or a fragment thereof, and in certain other further embodiments the composition induces in the patient a T lymphocyte that is capable of specifically recognizing a HE4a polypeptide having an amino acid sequence set forth in SEQ ID NO:11, or a fragment thereof. According to certain other embodiments, compositions and methods are provided that alter (e.g., increase or decrease in a statistically significant manner relative to an appropriate control) conception, contraception and/or fertility, comprising administering a HE4a polypeptide or fragment or variant thereof (including a fusion protein), or administering a composition comprising an immunoglobulin variable region that specifically binds to a HE4a polypeptide or fragment or variant thereof.

These and other aspects of the present invention will become evident upon reference to the following detailed description and attached drawings. In addition, various references are set forth herein which describe in more detail certain aspects of this invention, and are therefore incorporated by reference in their entireties.

BRIEF DESCRIPTION OF THE DRAWINGS

FIG. 4 depicts representative results of screening hybridoma supernatants and detection of HE4a-specific hybridoma antibodies using ELISA.

DETAILED DESCRIPTION OF THE INVENTION

Figure 1A:
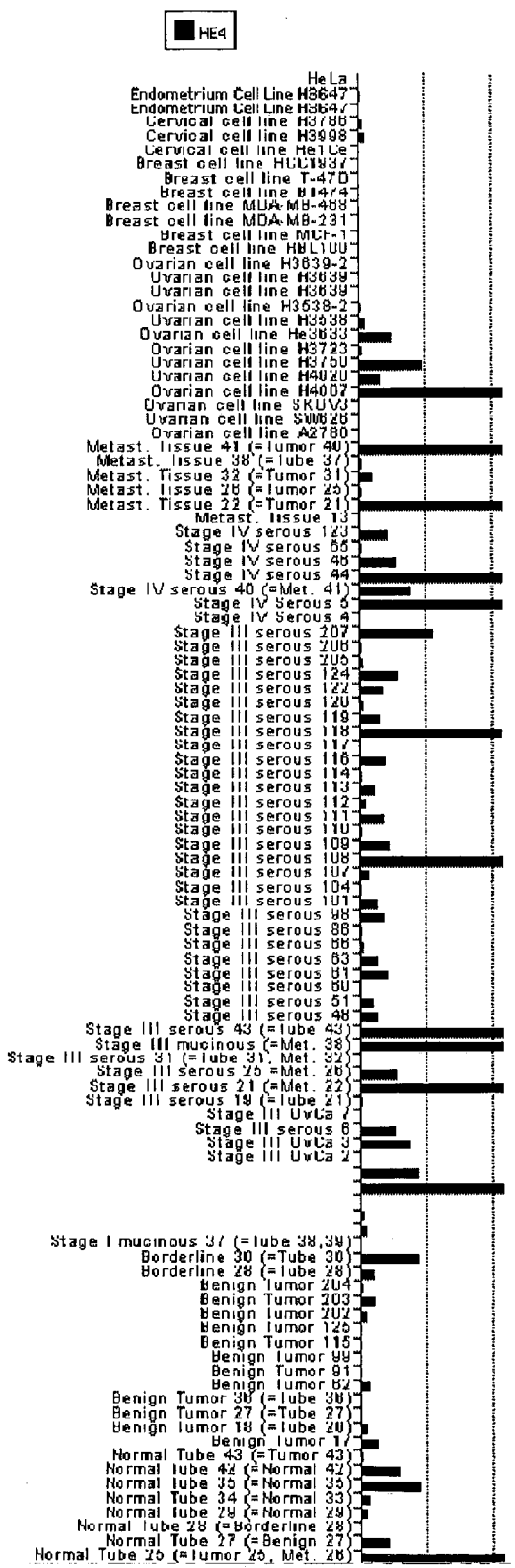
FIG. 1 shows real-time PCR detection of HE4a encoding cDNA in a panel of human samples.

The present invention pertains in part to the discovery of HE4a, a new member of the "four-disulfide core" family of proteins as described herein, which exhibits a sequence that is highly similar to, but distinct from, HE4 (Kirchhoff et al., 1991 *Biol. Reproduct.* 45:350-357). As described herein, HE4a (and not HE4) is most unexpectedly shown to be overexpressed in certain malignancies, for example in ovarian carcinomas, as well as in a number of other human tissues, in marked contrast to the restricted expression pattern of HE4 in human epididymal epithelial cells (Kirchhoff et al., 1991). The present invention also pertains in part to surprising advantages that derive from compositions and methods described herein, which provide detection of cell surface and/or soluble forms of certain gene products referred to herein as HE4a polypeptides that occur naturally in subjects, including elevated levels of such polypeptides in subjects having certain carcinomas (e.g., ovarian carcinomas). The invention therefore provides useful compositions and methods for the detection and diagnosis of a malignant condition in a subject by specific detection of such cell surface and/or soluble HE4a polypeptides.

As described in detail below, certain embodiments of the invention relate to HE4a polypeptides, which include soluble and cell surface forms of HE4a and HE4 polypeptides, including HE4 and HE4a polypeptide antigens and fusion proteins. In certain other embodiments, the invention relates to fragments, derivatives and/or analogs of HE4a polypeptides. Briefly, according to certain embodiments of the present invention, there is provided a method of screening for the presence of a malignant condition in a subject by contacting a biological sample from the subject with an antibody specific for a human HE4a polypeptide. The complete amino acid and nucleic acid coding sequences of HE4a polypeptides and HE4a-Ig fusion proteins are disclosed herein, including the surprising observation that a nucleic acid molecule derived from ovarian carcinoma cDNA encodes an expressed product having a sequence distinct from HE4 as described by Kirchhoff et al. (1991), and the further unexpected observation that whereas HE4 expression as disclosed by Kirchhoff et al. is limited to epididymal epithelial cells, HE4a expression according to the present disclosure is readily detectable in ovarian carcinomas.

As described herein, monoclonal antibodies that specifically recognize HE4a polypeptides are provided, such that those having ordinary skill in the art may routinely and without undue experimentation immunize a host and screen for HE4a polypeptide-specific antibody production using the present teachings along with methodologies well known in the art. For example, construction of recombinant HE4a expression vectors and host cells, including recombinant HE4a fusion proteins, is described herein and provides HE4a-specific antibodies.

From the physicochemical and immunochemical properties of HE4a polypeptides disclosed herein, and using the presently disclosed nucleic acid sequences encoding HE4a, a person having ordinary skill in the art may also prepare a recombinant HE4a polypeptide that can be used to produce and characterize specific antibodies according to well known methodologies. HE4a polypeptides can be expressed in mammalian cells, yeast, bacteria, or other cells under the control of appropriate promoters. Cell-free translation systems can also be employed to produce such proteins using RNAs derived from the HE4a polypeptide DNA coding regions disclosed herein. Appropriate cloning and expression vectors for use with prokaryotic and eukaryotic hosts are described by Sambrook et al., *Molecular Cloning: A Laboratory Manual*, Second Edition, Cold Spring Harbor, N.Y., (1989). In preferred embodiments of the invention, HE4a polypeptides are expressed in mammalian cells.

The nucleic acids of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. A coding sequence which encodes an HE4a polypeptide for use according to the invention may be identical to the coding sequences provided in SEQ ID NOS:3, 4, 6, 10 or 12 or may be a different coding sequence, which, as a result of the redundancy or degeneracy of the genetic code, encodes the same HE4a polypeptide as, for example, the cDNAs of SEQ ID NOS:10 and 12. The present invention therefore provides an isolated nucleic acid molecule that encodes a HE4a antigen polypeptide having the amino acid sequence of SEQ ID NOS:5, 7, 11 or 13, or a nucleic acid molecule capable of hybridizing to such an HE4a polypeptide-encoding nucleic acid, or a nucleic acid molecule having a sequence complementary thereto.

Variants preferably exhibit at least about 70% identity, more preferably at least about 80%-85% identity and most preferably at least about 90%, 92%, 94%, 95%, 96%, 97%, 98% or 99% identity to a polynucleotide sequence that encodes a native HE4a antigen polypeptide or a portion thereof, such as, for example, the nucleic acid sequences set forth in SEQ ID NOS:10 and 12. The percent identity may be readily determined by comparing sequences using computer algorithms well known to those of ordinary skill in the art, such as Align or the BLAST algorithm (Altschul, J. Mol. Biol. 219:555-565, 1991; Henikoff and Henikoff, Proc. Natl. Acad. Sci. USA 89:10915-10919, 1992), which is available at the NCBI website. Default parameters may be used.

Certain variants are substantially homologous to a native gene. Such polynucleotide variants are capable of hybridizing under moderately stringent conditions to a naturally occurring DNA or RNA sequence encoding a native HE4a antigen (or a complementary sequence). Suitable moderately stringent conditions include, for example, the following steps or their equivalent: prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS. For additional stringency, conditions may include, for example, a wash in 0.1×SSC and 0.1% SDS at 60° C. for 15 minutes, or the equivalent. A person having ordinary skill in the art will readily appreciate the parameters that may be varied as a routine matter to create appropriately stringent hybridization conditions that are in some way selective for a particular nucleic acid of interest, and will further appreciate that such conditions may be a function, inter alia, of the particular nucleic acid sequences involved in the hybridization, such as, for example, those disclosed herein as SEQ ID NOS:10 and 12, which encode HE4a polypeptides. See also, e.g., Ausubel et al., *Current Protocols in Molecular Biology*, Greene Publishing, 1995, regarding selection of nucleic acid hybridization conditions.

The nucleic acids which encode HE4a polypeptides, for example the human HE4a polypeptides having the amino acid sequences of SEQ ID NO:11 or any other HE4a polypeptides for use according to the invention, may include, but are not limited to: only the coding sequence for the HE4a polypeptide; the coding sequence for the HE4a polypeptide and additional coding sequence; the coding sequence for the HE4a polypeptide (and optionally additional coding sequence) and non-coding sequence, such as introns or non-coding sequences 5' and/or 3' of the coding sequence for the HE4a polypeptide, which for example may further include but need not be limited to one or more regulatory nucleic acid sequences that may be a regulated or regulatable promoter, enhancer, other transcription regulatory sequence, repressor binding sequence, translation regulatory sequence or any other regulatory nucleic acid sequence. Thus, the term "nucleic acid encoding an HE4a polypeptide" encompasses a nucleic acid which includes only coding sequence for the polypeptide as well as a nucleic acid which includes additional coding and/or non-coding sequence(s).

The present invention further relates to variants of the herein described nucleic acids which encode for fragments, analogs and derivatives of an HE4a polypeptide, for example the human HE4a polypeptides having the deduced amino acid sequence of SEQ ID NO:11. The variants of the nucleic acids encoding HE4a may be naturally occurring allelic variants of the nucleic acids or non-naturally occurring variants. As is known in the art, an allelic variant is an alternate form of a nucleic acid sequence which may have at least one of a substitution, a deletion or an addition of one or more nucleotides, any of which does not substantially alter the function of the encoded HE4a polypeptide. Thus, for example, the present invention includes nucleic acids encoding the same HE4a polypeptides as shown in SEQ ID NOS:5, 7 or 11, as well as variants of such nucleic acids, which variants may encode a fragment, derivative or analog of any of these polypeptides.

Variants and derivatives of HE4a may be obtained by mutations of nucleotide sequences encoding HE4a polypeptides. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making such alterations are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462.

Identification of nucleic acid molecules for use as antisense agents, which includes antisense oligonucleotides and ribozymes specific for nucleic acid sequences encoding HE4a polypeptides or variants or fragments thereof; and of DNA oligonucleotides encoding HE4a genes for targeted delivery for genetic therapy, involve methods well known in the art. For example, the desirable properties, lengths and other characteristics of such oligonucleotides are well known. In certain preferred embodiments such an antisense oligonucleotide comprises at least 15-30 consecutive nucleotides complementary to an isolated nucleic acid molecule encoding an HE4a polypeptide as provided herein, and in certain other preferred embodiments such an antisense oligonucleotide may comprise at least 31-50, 51-75, 76-125 or more consecutive nucleotides complementary to an isolated nucleic acid molecule encoding an HE4a polypeptide as provided herein. Antisense oligonucleotides are typically designed to resist degradation by endogenous nucleolytic enzymes by using such linkages as: phosphorothioate, methylphosphonate, sulfone, sulfate, ketyl, phosphorodithioate, phosphoramidate, phosphate esters, and other such linkages (see, e.g., Agrwal et al., *Tetrehedron Lett.* 28:3539-3542 (1987); Miller et al., *J. Am. Chem. Soc.* 93:6657-6665 (1971); Stec et al., *Tetrehedron Lett.* 26:2191-2194 (1985); Moody et al., *Nucl. Acids Res.* 12:4769-4782 (1989); Uznanski et al., *Nucl. Acids Res.* (1989); Letsinger et al., *Tetrahedron* 40:137-143 (1984); Eckstein, *Annu. Rev. Biochem.* 54:367-402 (1985); Eckstein, *Trends Biol. Sci.* 14:97-100 (1989); Stein In: *Oligodeoxynucleotides. Antisense Inhibitors of Gene Expression*, Cohen, Ed, Macmillan Press, London, pp. 97-117 (1989); Jager et al., *Biochemistry* 27:7237-7246 (1988)).

Antisense nucleotides are oligonucleotides that bind in a sequence-specific manner to nucleic acids, such as mRNA or DNA. When bound to mRNA that has complementary sequences, antisense prevents translation of the mRNA (see, e.g., U.S. Pat. No. 5,168,053 to Altman et al.; U.S. Pat. No. 5,190,931 to Inouye, U.S. Pat. No. 5,135,917 to Burch; U.S. Pat. No. 5,087,617 to Smith and Clusel et al. (1993) *Nucl. Acids Res.* 21:3405-3411, which describes dumbbell antisense oligonucleotides). Triplex molecules refer to single DNA strands that bind duplex DNA forming a colinear triplex molecule, thereby preventing transcription (see, e.g., U.S. Pat. No. 5,176,996 to Hogan et al., which describes methods for making synthetic oligonucleotides that bind to target sites on duplex DNA).

According to this embodiment of the invention, particularly useful antisense nucleotides and triplex molecules are molecules that are complementary to or bind the sense strand of DNA or mRNA that encodes an HE4a polypeptide such that inhibition of translation of mRNA encoding the HE4a polypeptide is effected.

A ribozyme is an RNA molecule that specifically cleaves RNA substrates, such as mRNA, resulting in specific inhibition or interference with cellular gene expression. There are at least five known classes of ribozymes involved in the cleavage and/or ligation of RNA chains. Ribozymes can be targeted to any RNA transcript and can catalytically cleave such transcripts (see, e.g., U.S. Pat. No. 5,272,262; U.S. Pat. No. 5,144,019; and U.S. Pat. Nos. 5,168,053, 5,180,818, 5,116,742 and 5,093,246 to Cech et al.). According to certain embodiments of the invention, any such HE4a mRNA-specific ribozyme, or a nucleic acid encoding such a ribozyme, may be delivered to a host cell to effect inhibition of HE4a gene expression. Ribozymes, and the like may therefore be delivered to the host cells by DNA encoding the ribozyme linked to a eukaryotic promoter, such as a eukaryotic viral promoter, such that upon introduction into the nucleus, the ribozyme will be directly transcribed.

Equivalent DNA constructs that encode various additions or substitutions of amino acid residues or sequences, or deletions of terminal or internal residues or sequences not needed for biological activity are also encompassed by the invention. For example, sequences encoding Cys residues that are not essential for biological activity can be altered to cause the Cys residues to be deleted or replaced with other amino acids, preventing formation of incorrect intramolecular disulfide bridges upon renaturation. Other equivalents can be prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

The appropriate DNA sequence(s) may be inserted into any of a number of well known vectors appropriate for the selected host cell by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 *Current Protocols in Molecular Biology*, Greene Publ. Assoc. Inc. & John Wiley & Sons, Inc., Boston, Mass.); Sambrook et al. (1989 *Molecular Cloning*, Second Ed., Cold Spring Harbor Laboratory, Plainview, N.Y.); and elsewhere.

Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived, for example, from SV40 splice and polyadenylation sites may be used to provide the required nontranscribed genetic elements. Introduction of the construct into the host cell can be effected by a variety of methods with which those skilled in the art will be familiar, including but not limited to, for example, calcium phosphate transfection, DEAE-Dextran mediated transfection, or electroporation (Davis et al., 1986 *Basic Methods in Molecular Biology*).

The present invention further relates to HE4a polypeptides and in particular to methods for detecting a malignant condition. In a preferred embodiment, malignancy is detected by determining the presence in a biological sample of a naturally occurring soluble molecule, or in a sample comprising a cell the presence of a cell surface molecule, having an antigenic determinant reactive with at least one antibody specific for a HE4a polypeptide. In another preferred embodiment, malignancy is detected by determining the presence in a biological sample of at least one naturally occurring HE4a polypeptide. As provided herein, a "HE4a antigen polypeptide" or "HE4a polypeptide" includes any polypeptide having an amino acid sequence of SEQ ID NO:11, including any fragment, derivative or analog thereof, and also includes any polypeptide encoded by a nucleic acid molecule comprising SEQ ID NO:10 or 12, or by a nucleic acid molecule capable of hybridizing to a nucleic acid molecule of SEQ ID NO:10 or 12, or a fragment, derivative or analog thereof. Certain preferred embodiments of the present invention contemplate compositions and methods directed to HE4a sequences as provided herein (e.g., SEQ ID NOS:10-13) but which expressly exclude, on the basis of differences in structure, function and/or cell type expression or tissue distribution, or the like (including antibody-defined detectable epitopes and also including oligonucleotide-defined hybridization detection), HE4 sequences disclosed in Kirchoff et al. (e.g., 1991 Biol. Reproduct. 45:350; SEQ ID NOS:8-9).

The HE4a polypeptide of the invention may be an unmodified polypeptide or may be a polypeptide that has been posttranslationally modified, for example by glycosylation, phosphorylation, fatty acylation including glycosylphosphatidylinositol anchor modification or the like, phospholipase cleavage such as phosphatidylinositol-specific phospholipase c mediated hydrolysis or the like, protease cleavage, dephosphorylation or any other type of protein posttranslational modification such as a modification involving formation or cleavage of a covalent chemical bond.

The terms "fragment," "derivative" and "analog" when referring to HE4a polypeptides, HE4a antigen polypeptides or HE4a fusion proteins, refers to any HE4a polypeptide that retains essentially the same biological function and/or activity as such polypeptide. Thus, an analog may include a HE4a antigen polypeptide isoform such as a differentially post-translationally modified HE4a polypeptide or a variant such as a splice variant. As is well known in the art, a "splice variant" includes variant or alternative forms of a polypeptide that arise from the differential intracellular processing of an RNA transcript. For example, two distinct mRNA species may be splice variants of one another where they differ only by the inclusion of all or a portion of a sequence corresponding to a particular exon in one mRNA species and its absence from the other species. As those familiar with the art will appreciate, other structural relationships can exist between mRNA species that would be generally regarded as splice variants. A HE4a polypeptide further includes a proprotein which can be activated by cleavage of the proprotein portion to produce an active HE4a polypeptide.

Biological functions and/or activities of fragments, derivatives and analogs of HE4a polypeptides or of HE4a antigen polypeptides include, but need not be limited to, the use of such polypeptides as markers in a method of screening for the presence of a malignant condition in a subject as disclosed herein. For example, by detecting in a sample from the subject a molecule naturally occurring in soluble form and having an antigenic determinant that is reactive with at least one antibody specific for a HE4a polypeptide, one skilled in the art may be monitoring a biological function and/or activity of an HE4a polypeptide. Further, it should be noted that in certain embodiments the subject invention method of screening is directed to comparing relative quantities, levels and/or amounts of a detectable molecule naturally occurring in soluble form and having an antigenic determinant that is reactive with at least one antibody specific for a HE4a polypeptide in each of (i) a first biological sample from a first subject suspected of having a malignant condition, and (ii) a second biological sample from a second subject known to be free of a malignant condition. Accordingly, the relative quantitative presence of a HE4a polypeptide in a biological sample may be a biological function and/or activity of a HE4a polypeptide, although such function and/or activity should not be so limited.

A fragment, derivative or analog of a HE4a polypeptide may be (i) one in which one or more of the amino acid residues are substituted with a conserved or non-conserved amino acid residue (preferably a conserved amino acid residue); (ii) one in which additional amino acids are fused to the HE4a polypeptide, including amino acids that may be employed for purification of the HE4a polypeptide or a proprotein sequence; or (iii) a truncated HE4a polypeptide. Such fragments, derivatives and analogs are deemed to be within the scope of those skilled in the art from the teachings herein.

A truncated HE4a polypeptide may be any HE4a polypeptide molecule that comprises less than a full length version of the HE4a polypeptide. Truncated molecules provided by the present invention may include truncated biological polymers, and in preferred embodiments of the invention such truncated molecules may be truncated nucleic acid molecules or truncated polypeptides. Truncated nucleic acid molecules have less than the full length nucleotide sequence of a known or described nucleic acid molecule, where such a known or described nucleic acid molecule may be a naturally occurring, a synthetic or a recombinant nucleic acid molecule, so long as one skilled in the art would regard it as a full length molecule. Thus, for example, truncated nucleic acid molecules that correspond to a gene sequence contain less than the full length gene where the gene comprises coding and non-coding sequences, promoters, enhancers and other regulatory sequences, flanking sequences and the like, and other functional and non-functional sequences that are recognized as part of the gene. In another example, truncated nucleic acid molecules that correspond to a mRNA sequence contain less than the full length mRNA transcript, which may include various translated and non-translated regions as well as other functional and non-functional sequences. In other preferred embodiments, truncated molecules are polypeptides that comprise less than the full length amino acid sequence of a particular protein.

As used herein "deletion" has its common meaning as understood by those familiar with the art, and may refer to molecules that lack one or more of a portion of a sequence from either terminus or from a non-terminal region, relative to a corresponding full length molecule, for example, as in the case of truncated molecules provided herein. Truncated molecules that are linear biological polymers such as nucleic acid molecules or polypeptides may have one or more of a deletion from either terminus of the molecule or a deletion from a non-terminal region of the molecule, where such deletions may be deletions of 1-1500 contiguous nucleotide or amino acid residues, preferably 1-500 contiguous nucleotide or amino acid residues and more preferably 1-300 contiguous nucleotide or amino acid residues.

As known in the art "similarity" between two polypeptides is determined by comparing the amino acid sequence and conserved amino acid substitutes thereto of the polypeptide to the sequence of a second polypeptide. Similarity between two polypeptide or nucleotide sequences, or even the percent identity, may be readily determined by comparing sequences using computer algorithms well known to those of ordinary skill in the art, such as the BLAST algorithm (Altschul, J. Mol. Biol. 219:555-565, 1991; Henikoff and Henikoff, Proc. Natl. Acad. Sci. USA 89:10915-10919, 1992), which is available at the NCBI website. Default parameters may be used. Examples of other useful computer algorithms are those used in programs such as Align and FASTA, which may be accessed, for example, at the Genestream internet website of the Institut de Genetique Humaine, Montpellier, France and used with default parameters. Fragments or portions of the polypeptides of the present invention may be employed for producing the corresponding full-length polypeptide by peptide synthesis; therefore, the fragments may be employed as intermediates for producing the full-length polypeptides.

The term "isolated" means that the material is removed from its original environment (e.g., the natural environment if it is naturally occurring). For example, a naturally occurring polypeptide or polynucleotide present in a living animal is not isolated, but the same polypeptide or polynucleotide, separated from some or all of the co-existing materials in the natural system, is isolated. Such polypeptides or polynucleotides could be part of a composition, and still be isolated in that such composition is not part of its natural environment.

Affinity techniques are particularly useful in the context of isolating HE4a polypeptides for use according to the methods of the present invention, and may include any method that exploits a specific binding interaction with a HE4a polypeptide to effect a separation. For example, because HE4a polypeptides may contain covalently attached oligosaccharide moieties (see, e.g., FIG. 2 as described in the Examples), an affinity technique such as binding of a HE4a polypeptide to a suitable immobilized lectin under conditions that permit carbohydrate binding by the lectin may be a particularly useful affinity technique. Other useful affinity techniques include immunological techniques for isolating a HE4a polypeptide, which techniques rely on specific binding interaction between antibody combining sites for antigen and antigenic determinants present in the complexes. Immunological techniques include, but need not be limited to, immunoaffinity chromatography, immunoprecipitation, solid phase immunoadsorption or other immunoaffinity methods. For these and other useful affinity techniques, see, for example, Scopes, R. K., *Protein Purification: Principles and Practice*, 1987, Springer-Verlag, NY; Weir, D. M., *Handbook of Experimental Immunology*, 1986, Blackwell Scientific, Boston; and Hermanson, G. T. et al., *Immobilized Affinity Ligand Techniques*, 1992, Academic Press, Inc., California; which are hereby incorporated by reference in their entireties, for details regarding techniques for isolating and characterizing complexes, including affinity techniques.

As described herein, the invention provides a fusion protein comprising a polypeptide fused to a HE4a. Such HE4a fusion proteins are encoded by nucleic acids that have the HE4a coding sequence fused in frame to an additional coding sequence to provide for expression of a HE4a polypeptide sequence fused to an additional functional or non-functional polypeptide sequence that permits, for example by way of illustration and not limitation, detection, isolation and/or purification of the HE4a fusion protein. Such HE4a fusion proteins may permit detection, isolation and/or purification of the HE4a fusion protein by protein-protein affinity, metal affinity or charge affinity-based polypeptide purification, or by specific protease cleavage of a fusion protein containing a fusion sequence that is cleavable by a protease such that the HE4a polypeptide is separable from the fusion protein.

Thus, HE4a fusion proteins may comprise affinity tag polypeptide sequences, which refers to polypeptides or peptides added to HE4a to facilitate detection and isolation of the HE4a via a specific affinity interaction with a ligand. The ligand may be any molecule, receptor, counterreceptor, antibody or the like with which the affinity tag may interact through a specific binding interaction as provided herein. Such peptides include, for example, poly-His or the antigenic identification peptides described in U.S. Pat. No. 5,011,912 and in Hopp et al., (1988 *Bio/Technology* 6:1204), or the XPRESS™ epitope tag (Invitrogen, Carlsbad, Calif.). The affinity sequence may be a hexa-histidine tag as supplied, for example, by a pBAD/His (Invitrogen) or a pQE-9 vector to provide for purification of the mature polypeptide fused to the marker in the case of a bacterial host, or, for example, the affinity sequence may be a hemagglutinin (HA) tag when a mammalian host, e.g., COS-7 cells, is used. The HA tag corresponds to an antibody defined epitope derived from the influenza hemagglutinin protein (Wilson et al., 1984 *Cell* 37:767).

HE4a fusion proteins may, in particularly preferred embodiments and as described in greater detail below, further comprise immunoglobulin constant region polypeptides added to HE4a to facilitate detection, isolation and/or localization of HE4a. The immunoglobulin constant region polypeptide preferably is fused to the C-terminus of a HE4a polypeptide. According to non-limiting theory, inclusion of immunoglobulin (Ig) constant region domains in HE4a fusion proteins as provided herein may offer advantages, for example, those associated with the immunogenic/non-immunogenic properties of particular Ig regions when used in particular hosts (i.e., "self" vs. "non-self"), or those which facilitate isolation and/or detection of a fusion protein. These and other advantages of Ig fusion proteins will be appreciated by those familiar with the art, based on the present disclosure. General preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990). A gene fusion encoding the HE4a:Fc fusion protein is inserted into an appropriate expression vector. In certain embodiments of the invention, HE4a:Fc fusion proteins may be allowed to assemble much like antibody molecules, whereupon interchain disulfide bonds form between Fc polypeptides, yielding dimeric HE4a fusion proteins.

HE4a fusion proteins having specific binding affinities for pre-selected antigens by virtue of fusion polypeptides comprising immunoglobulin V-region domains encoded by DNA sequences linked in-frame to sequences encoding HE4a are also within the scope of the invention, including variants and fragments thereof as provided herein. General strategies for the construction of fusion proteins having immunoglobulin V-region fusion polypeptides are disclosed, for example, in EP 0318554; U.S. Pat. No. 5,132,405; U.S. Pat. No. 5,091,513; and U.S. Pat. No. 5,476,786.

The nucleic acid of the present invention may also encode a fusion protein comprising a HE4a polypeptide fused to other polypeptides having desirable affinity properties, for example an enzyme such as glutathione-S-transferase. As another example, HE4a fusion proteins may also comprise a HE4a polypeptide fused to a *Staphylococcus aureus* protein A polypeptide; protein A encoding nucleic acids and their use in constructing fusion proteins having affinity for immunoglobulin constant regions are disclosed generally, for example, in U.S. Pat. No. 5,100,788. Other useful affinity polypetides for construction of HE4a fusion proteins may include streptavidin fusion proteins, as disclosed, for example, in WO 89/03422; U.S. Pat. No. 5,489,528; U.S. Pat. No. 5,672,691; WO 93/24631; U.S. Pat. No. 5,168,049; U.S. Pat. No. 5,272,254 and elsewhere, and avidin fusion proteins (see, e.g., EP 511,747). As provided herein and in the cited references, HE4a polypeptide sequences may be fused to fusion polypeptide sequences that may be full length fusion polypeptides and that may alternatively be variants or fragments thereof.

The present invention also contemplates HE4a fusion proteins that contain polypeptide sequences that direct the fusion protein to the cell nucleus, to reside in the lumen of the endoplasmic reticulum (ER), to be secreted from a cell via the classical ER-Golgi secretory pathway (see, e.g., von Heijne, *J. Membrane Biol.* 115:195-201, 1990), to be incorporated into the plasma membrane, to associate with a specific cytoplasmic component including the cytoplasmic domain of a transmembrane cell surface receptor or to be directed to a particular subcellular location by any of a variety of known intracellular protein sorting mechanisms with which those skilled in the art will be familiar (See, e.g., Rothman, *Nature* 372:55-63, 1994, Adrani et al., 1998 *J. Biol. Chem.* 273:10317, and references cited therein.). Accordingly, these and related embodiments are encompassed by the instant compositions and methods directed to targeting a polypeptide of interest to a predefined intracellular, membrane or extracellular localization.

The present invention also relates to vectors and to constructs that include nucleic acids of the present invention, and in particular to "recombinant expression constructs" that include any nucleic acids encoding HE4a polypeptides according to the invention as provided above; to host cells which are genetically engineered with vectors and/or constructs of the invention and to the production of HE4a polypeptides and fusion proteins of the invention, or fragments or variants thereof, by recombinant techniques. HE4a proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described, for example, by Sambrook, et al., *Molecular Cloning: A Laboratory Manual*, Second Edition, Cold Spring Harbor, N.Y., (1989).

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression constructs for bacterial use are constructed by inserting into an expression vector a structural DNA sequence encoding a desired protein together with suitable translation initiation and termination signals in operable reading phase with a functional promoter. The construct may comprise one or more phenotypic selectable markers and an origin of replication to ensure maintenance of the vector construct and, if desirable, to provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice. Any other plasmid or vector may be used as long as they are replicable and viable in the host.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter, if it is a regulated promoter as provided herein, is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents; such methods are well know to those skilled in the art.

Thus, for example, the nucleic acids of the invention as provided herein may be included in any one of a variety of expression vector constructs as a recombinant expression construct for expressing a HE4a polypeptide. Such vectors and constructs include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA, such as vaccinia, adenovirus, fowl pox virus, and pseudorabies. However, any other vector may be used for preparation of a recombinant expression construct as long as it is replicable and viable in the host.

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 *Current Protocols in Molecular Biology*, Greene Publ. Assoc. Inc. & John Wiley & Sons, Inc., Boston, Mass.); Sambrook et al. (1989 *Molecular Cloning*, Second Ed., Cold Spring Harbor Laboratory, Plainview, N.Y.); Maniatis et al. (1982 Molecular Cloning, Cold Spring Harbor Laboratory, Plainview, N.Y.); and elsewhere.

The DNA sequence in the expression vector is operatively linked to at least one appropriate expression control sequences (e.g., a promoter or a regulated promoter) to direct mRNA synthesis. Representative examples of such expression control sequences include LTR or SV40 promoter, the *E. coli* lac or trp, the phage lambda PL promoter and other promoters known to control expression of genes in prokaryotic or eukaryotic cells or their viruses. Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter or regulated promoter operably linked to a nucleic acid encoding a HE4a polypeptide is described herein.

As noted above, in certain embodiments the vector may be a viral vector such as a retroviral vector. For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

The viral vector includes one or more promoters. Suitable promoters which may be employed include, but are not limited to, the retroviral LTR; the SV40 promoter; and the human cytomegalovirus (CMV) promoter described in Miller, et al., *Biotechniques* 7:980-990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein, and may be from among either regulated promoters or promoters as described above.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+en-vAm12, and DAN cell lines as described in Miller, *Human Gene Therapy*, 1:5-14 (1990), which is incorporated herein by reference in its entirety. The vector may transduce the packaging cells through any means known in the art. Such means include, but are not limited to, electroporation, the use of liposomes, and calcium phosphate precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the HE4a polypeptides or fusion proteins. Such retroviral vector particles then may be employed, to transduce eukaryotic cells, either in vitro or in vivo. The transduced eukaryotic cells will express the nucleic acid sequence(s) encoding the HE4a polypeptide or fusion protein. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, bronchial epithelial cells and various other culture-adapted cell lines.

As another example of an embodiment of the invention in which a viral vector is used to prepare the recombinant HE4a expression construct, in one preferred embodiment, host cells transduced by a recombinant viral construct directing the expression of HE4a polypeptides or fusion proteins may produce viral particles containing expressed HE4a polypeptides or fusion proteins that are derived from portions of a host cell membrane incorporated by the viral particles during viral budding. In another preferred embodiment, HE4a encoding nucleic acid sequences are cloned into a baculovirus shuttle vector, which is then recombined with a baculovirus to generate a recombinant baculovirus expression construct that is used to infect, for example, Sf9 host cells, as described in *Baculovirus Expression Protocols, Methods in Molecular Biology* Vol. 39, C. D. Richardson, Editor, Human Press, Totowa, N.J., 1995; Piwnica-Worms, "Expression of Proteins in Insect Cells Using Baculoviral Vectors," Section II in Chapter 16 in: *Short Protocols in Molecular Biology*, 2nd Ed., Ausubel et al., eds., John Wiley & Sons, New York, N.Y., 1992, pages 16-32 to 16-48.

In another aspect, the present invention relates to host cells containing the above described recombinant HE4a expression constructs. Host cells are genetically engineered (transduced, transformed or transfected) with the vectors and/or expression constructs of this invention which may be, for example, a cloning vector, a shuttle vector or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding HE4a polypeptides or HE4a fusion proteins. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as *E. coli, Streptomyces, Salmonella typhimurium*; fungal cells, such as yeast; insect cells, such as *Drosophila* S2 and *Spodoptera* Sf9; animal cells, such as CHO, COS or 293 cells; adenoviruses; plant cells, or any suitable cell already adapted to in vitro propagation or so established de novo. The selection of an appropriate host is deemed to be within the scope of those skilled in the art from the teachings herein.

Various mammalian cell culture systems can also be employed to express recombinant protein. The invention is therefore directed in part to a method of producing a recombinant HE4a polypeptide, by culturing a host cell comprising a recombinant expression construct that comprises at least one promoter operably linked to a nucleic acid sequence encoding a HE4a. In certain embodiments, the promoter may be a regulated promoter as provided herein, for example a tetracylcine-repressible promoter. In certain embodiments the recombinant expression construct is a recombinant viral expression construct as provided herein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of MRA expression constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, calcium phosphate transfection, DEAE-Dextran mediated transfection, or electroporation (Davis et al., 1986 *Basic Methods in Molecular Biology*).

The expressed recombinant HE4a antigen polypeptides (or HE4a polypeptides), or fusion proteins derived therefrom, may be useful as immunogens in the form of intact host cells; intact organelles such as cell membranes, intracellular vesicles or other cellular organelles; or disrupted cell preparations including but not limited to cell homogenates or lysates, uni- and multilamellar membrane vesicles or other preparations. Alternatively, expressed recombinant mesothelin related antigen polypeptides (or mesothelin polypeptides) or fusion proteins can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography including immunoaffinity chromatography, hydroxylapatite chromatography and lectin chromatography. Protein refolding steps can be used, as necessary, in completing configuration of the mature protein. Finally, high performance liquid chromatography (HPLC) can be employed for final purification steps. Expressed recombinant HE4a antigen polypeptides (or HE4a polypeptides) or fusion proteins may also be useful as target antigens in any of a number of assay configurations for routine antibody screening, which can be readily performed by those having ordinary skill in the art.

The HE4a antigen polypeptide (or HE4a polypeptide) that is an immunogen for the production of a specific antibody to be used in the method of the present invention may thus be a naturally purified product, or a product of chemical synthetic procedures, or produced by recombinant techniques from a prokaryotic or, preferably, a eukaryotic host. Depending upon the host employed in a recombinant production procedure, the polypeptides of the present invention may be glycosylated or otherwise posttranslationally modified as known in the art and as provided herein.

According to the present invention, a soluble human HE4a antigen polypeptide (or HE4a polypeptide) may be detected in a biological sample from a subject or biological source. Biological samples may be provided by obtaining a blood sample, biopsy specimen, tissue explant, organ culture, biological fluid or any other tissue or cell preparation from a subject or a biological source. The subject or biological source may be a human or non-human animal, a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines and the like. In certain preferred embodiments of the invention, the subject or biological source may be suspected of having or being at risk for having a malignant condition, which in certain further preferred embodiments may be an ovarian cancer such as ovarian carcinoma, and in certain other preferred embodiments of the invention the subject or biological source may be known to be free of a risk or presence of such disease.

In certain preferred embodiments the biological sample comprises at least one cell from a subject or biological source, and in certain other preferred embodiments the biological sample is a biological fluid containing a soluble human mesothelin related antigen polypeptide. Biological fluids are typically liquids at physiological temperatures and may include naturally occurring fluids present in, withdrawn from, expressed or otherwise extracted from a subject or biological source. Certain biological fluids derive from particular tissues, organs or localized regions and certain other biological fluids may be more globally or systemically situated in a subject or biological source. Examples of biological fluids include blood, serum and serosal fluids, plasma, lymph, urine, cerebrospinal fluid, saliva, mucosal secretions of the secretory tissues and organs, vaginal secretions, ascites fluids such as those associated with non-solid tumors, fluids of the pleural, pericardial, peritoneal, abdominal and other body cavities, and the like. Biological fluids may also include liquid solutions contacted with a subject or biological source, for example, cell and organ culture medium including cell or organ conditioned medium, lavage fluids and the like. In certain highly preferred embodiments the biological sample is serum, and in certain other highly preferred embodiments the biological sample is plasma. In other preferred embodiments the biological sample is a cell-free liquid solution.

In certain other preferred embodiments the biological sample comprises an intact cell, and in certain other preferred embodiments the biological sample comprises a cell extract containing a nucleic acid sequence encoding a HE4a antigen polypeptide having the amino acid sequence set forth in SEQ ID NOS:11 or 13, or a fragment or variant thereof.

A "molecule naturally occurring in soluble form" in a sample may be a soluble protein, polypeptide, peptide, amino acid, or derivative thereof; a lipid, fatty acid or the like, or derivative thereof; a carbohydrate, saccharide or the like or derivative thereof, a nucleic acid, nucleotide, nucleoside, purine, pyrimidine or related molecule, or derivative thereof, or the like; or any combination thereof such as, for example, a glycoprotein, a glycolipid, a lipoprotein, a proteolipid, or any other biological molecule that is a soluble or cell-free constituent of a biological sample as provided herein. A "molecule naturally occurring in soluble form" further refers to a molecule that is in solution or present in a biological sample, including a biological fluid as provided herein, and that is not bound to the surface of an intact cell. For example, a molecule naturally occurring in soluble form may include but need not be limited to a solute; a component of a macromolecular complex; a material that is shed, secreted or exported from a cell; a colloid; a microparticle or nanoparticle or other fine suspension particle; or the like.

The presence of a malignant condition in a subject refers to the presence of dysplastic, cancerous and/or transformed cells in the subject, including, for example neoplastic, tumor, non-contact inhibited or oncogenically transformed cells, or the like. By way of illustration and not limitation, in the context of the present invention a malignant condition may refer further to the presence in a subject of cancer cells that are capable of secreting, shedding, exporting or releasing a HE4a antigen polypeptide (or a HE4a polypeptide) in such a manner that elevated levels of such a polypeptide are detectable in a biological sample from the subject. In preferred embodiments, for example, such cancer cells are malignant epithelial cells such as carcinoma cells, and in particularly preferred embodiments such cancer cells are malignant mesothelioma cells, which are transformed variants of squamous cell epithelial or mesothelial cells that are found, for example, lining pleural, pericardial, peritoneal, abdominal and other body cavities.

In the most preferred embodiments of the invention, tumor cells, the presence of which signifies the presence of a malignant condition, are ovarian carcinoma cells, including primary and metastatic ovarian carcinoma cells. Criteria for classifying a malignancy as ovarian carcinoma are well known in the art (see, e.g., Bell et al., 1998 Br. J. Obstet. Gynaecol. 105:1136; Meier et al., 1997 Anticancer Res. 17(4B):3019; Meier et al. 1997 Anticancer Res. 17(4B): 2949; Cioffi et al., 1997 Tumori 83:594; and references cited therein) as are the establishment and characterization of human ovarian carcinoma cell lines from primary and metastatic tumors (e.g., OVCAR-3, Amer. Type Culture Collection, Manassas, Va.; Yuan et al., 1997 Gynecol. Oncol. 66:378). In other embodiments, the malignant condition may be mesothelioma, pancreatic carcinoma, non-small cell lung carcinoma or another form of cancer, including any of the various carcinomas such as squamous cell carcinomas and adenocarcinomas, and also including sarcomas and hematologic malignancies (e.g., leukemias, lymphomas, myelomas, etc.). Classification of these and other malignant conditions is known to those having familiarity with the art, and the present disclosure provides determination of the presence of a HE4a polypeptide in such a malignant condition without undue experimentation.

As provided herein, the method of screening for the presence of a malignant condition in a subject may feature the use of an antibody specific for a HE4a antigen polypeptide or an antibody specific for a HE4a polypeptide.

Antibodies that are specific for a HE4a antigen polypeptide (or a HE4a polypeptide) are readily generated as monoclonal antibodies or as polyclonal antisera, or may be produced as genetically engineered immunoglobulins (Ig) that are designed to have desirable properties using methods well known in the art. For example, by way of illustration and not limitation, antibodies may include recombinant IgGs, chimeric fusion proteins having immunoglobulin derived sequences or "humanized" antibodies (see, e.g., U.S. Pat. Nos. 5,693,762; 5,585,089; 4,816,567; 5,225,539; 5,530,101; and references cited therein) that may all be used for detection of a human HE4a polypeptide according to the invention. Such antibodies may be prepared as provided herein, including by immunization with HE4a polypeptides as described below. For example, as provided herein, nucleic acid sequences encoding HE4a polypeptides are disclosed, such that those skilled in the art may routinely prepare these polypeptides for use as immunogens. For instance, monoclonal antibodies such as 2H5, 3D8 and 4H4, which are described in greater detail below, may be used to practice certain methods according to the present invention.

The term "antibodies" includes polyclonal antibodies, monoclonal antibodies, fragments thereof such as F(ab')$_2$, and Fab fragments, as well as any naturally occurring or recombinantly produced binding partners, which are molecules that specifically bind a HE4a polypeptide. Antibodies are defined to be "immunospecific" or specifically binding if they bind HE4a polypeptide with a $K_a$ of greater than or equal to about $10^4$ $M^{-1}$, preferably of greater than or equal to about $10^5$ $M^{-1}$, more preferably of greater than or equal to about $10^6$ $M^{-1}$ and still more preferably of greater than or equal to about $10^7$ $M^{-1}$. Affinities of binding partners or antibodies can be readily determined using conventional techniques, for example those described by Scatchard et al., Ann. N.Y. Acad. Sci. 51:660 (1949). Determination of other proteins as binding partners of a HE4a polypeptide can be performed using any of a number of known methods for identifying and obtaining proteins that specifically interact with other proteins or polypeptides, for example, a yeast two-hybrid screening system such as that described in U.S. Pat. No. 5,283,173 and U.S. Pat. No. 5,468,614, or the equivalent. The present invention also includes the use of a HE4a polypeptide, and peptides based on the amino acid sequence of a HE4a polypeptide, to prepare binding partners and antibodies that specifically bind to a HE4a polypeptide.

Antibodies may generally be prepared by any of a variety of techniques known to those of ordinary skill in the art (see, e.g., Harlow and Lane, Antibodies: A Laboratory Manual, Cold Spring Harbor Laboratory, 1988). In one such technique, an immunogen comprising a HE4a polypeptide, for example a cell having a HE4a polypeptide on its surface or an isolated HE4a polypeptide is initially injected into a suitable animal (e.g., mice, rats, rabbits, sheep and goats), preferably according to a predetermined schedule incorporating one or more booster immunizations, and the animals are bled periodically. Polyclonal antibodies specific for the HE4a polypeptide may then be purified from such antisera by, for example, affinity chromatography using the polypeptide coupled to a suitable solid support.

Monoclonal antibodies specific for HE4a polypeptides or variants thereof may be prepared, for example, using the technique of Kohler and Milstein (1976 Eur. J. Immunol. 6:511-519), and improvements thereto. Briefly, these methods involve the preparation of immortal cell lines capable of producing antibodies having the desired specificity (i.e., reactivity with the mesothelin polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. For example, the spleen cells and myeloma cells may be combined with a membrane fusion promoting agent such as polyethylene glycol or a nonionic detergent for a few minutes, and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred. Hybridomas that generate monoclonal antibodies that specifically bind to HE4a polypeptides are contemplated by the present invention.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. For example, antibodies may be purified by chromatography on immobilized Protein G or Protein A using standard techniques.

Within certain embodiments, the use of antigen-binding fragments of antibodies may be preferred. Such fragments include Fab fragments, which may be prepared using standard techniques (e.g., by digestion with papain to yield Fab and Fc fragments). The Fab and Fc fragments may be separated by affinity chromatography (e.g., on immobilized protein A columns), using standard techniques. See, e.g., Weir, D. M., Handbook of Experimental Immunology, 1986, Blackwell Scientific, Boston.

Multifunctional fusion proteins having specific binding affinities for pre-selected antigens by virtue of immunoglobulin V-region domains encoded by DNA sequences linked in-frame to sequences encoding various effector proteins are known in the art, for example, as disclosed in EP-B1-0318554, U.S. Pat. No. 5,132,405, U.S. Pat. No. 5,091,513 and U.S. Pat. No. 5,476,786. Such effector proteins include polypeptide domains that may be used to detect binding of the fusion protein by any of a variety of techniques with which those skilled in the art will be familiar, including but not limited to a biotin mimetic sequence (see, e.g., Luo et al., 1998 *J. Biotechnol.* 65:225 and references cited therein), direct covalent modification with a detectable labeling moiety, non-covalent binding to a specific labeled reporter molecule, enzymatic modification of a detectable substrate or immobilization (covalent or non-covalent) on a solid-phase support.

Single chain antibodies for use in the present invention may also be generated and selected by a method such as phage display (see, e.g., U.S. Pat. No. 5,223,409; Schlebusch et al., 1997 *Hybridoma* 16:47; and references cited therein). Briefly, in this method, DNA sequences are inserted into the gene III or gene VIII gene of a filamentous phage, such as M13. Several vectors with multicloning sites have been developed for insertion (McLafferty et al., *Gene* 128: 29-36, 1993; Scott and Smith, *Science* 249:386-390, 1990; Smith and Scott, *Methods Enzymol.* 217:228-257, 1993). The inserted DNA sequences may be randomly generated or may be variants of a known binding domain for binding to a HE4a polypeptide. Single chain antibodies may readily be generated using this method. Generally, the inserts encode from 6 to 20 amino acids. The peptide encoded by the inserted sequence is displayed on the surface of the bacteriophage. Bacteriophage expressing a binding domain for a HE4a polypeptide are selected by binding to an immobilized HE4a polypeptide, for example a recombinant polypeptide prepared using methods well known in the art and nucleic acid coding sequences as disclosed herein. Unbound phage are removed by a wash, typically containing 10 mM Tris, 1 mM EDTA, and without salt or with a low salt concentration. Bound phage are eluted with a salt containing buffer, for example. The NaCl concentration is increased in a step-wise fashion until all the phage are eluted. Typically, phage binding with higher affinity will be released by higher salt concentrations. Eluted phage are propagated in the bacteria host. Further rounds of selection may be performed to select for a few phage binding with high affinity. The DNA sequence of the insert in the binding phage is then determined. Once the predicted amino acid sequence of the binding peptide is known, sufficient peptide for use herein as an antibody specific for a HE4a polypeptide may be made either by recombinant means or synthetically. Recombinant means are used when the antibody is produced as a fusion protein. The peptide may also be generated as a tandem array of two or more similar or dissimilar peptides, in order to maximize affinity or binding.

To detect an antigenic determinant reactive with an antibody specific for a HE4a polypeptide, the detection reagent is typically an antibody, which may be prepared as described herein. There are a variety of assay formats known to those of ordinary skill in the art for using an antibody to detect a polypeptide in a sample, including but not limited to enzyme linked immunosorbent assay (ELISA), radioimmunoassay (RIA), immunofluorimetry, immunoprecipitation, equilibrium dialysis, immunodiffusion and other techniques. See, e.g., Harlow and Lane, *Antibodies: A Laboratory Manual*, Cold Spring Harbor Laboratory, 1988; Weir, D. M., *Handbook of Experimental Immunology*, 1986, Blackwell Scientific, Boston. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as is well known in the art and described below.

In another embodiment, the assay involves the use of an antibody immobilized on a solid support to bind to the target HE4a polypeptide and remove it from the remainder of the sample. The bound HE4a polypeptide may then be detected using a second antibody reactive with a distinct HE4a polypeptide antigenic determinant, for example, a reagent that contains a detectable reporter moiety. As a non-limiting example, according to this embodiment the immobilized antibody and the second antibody which recognize distinct antigenic determinants may be any two of the monoclonal antibodies described herein selected from the monoclonal antibodies 2H5, 3D8 and 4H4. Alternatively, a competitive assay may be utilized, in which a HE4a polypeptide is labeled with a detectable reporter moiety and allowed to bind to the immobilized HE4a polypeptide specific antibody after incubation of the immobilized antibody with the sample. The extent to which components of the sample inhibit the binding of the labeled polypeptide to the antibody is indicative of the reactivity of the sample with the immobilized antibody, and as a result, indicative of the level of HE4a in the sample.

The solid support may be any material known to those of ordinary skill in the art to which the antibody may be attached, such as a test well in a microtiter plate, a nitrocellulose filter or another suitable membrane. Alternatively, the support may be a bead or disc, such as glass, fiberglass, latex or a plastic such as polystyrene or polyvinylchloride. The antibody may be immobilized on the solid support using a variety of techniques known to those in the art, which are amply described in the patent and scientific literature.

In certain preferred embodiments, the assay for detection of HE4a antigen polypeptide in a sample is a two-antibody sandwich assay. This assay may be performed by first contacting a HE4a polypeptide-specific antibody (e.g., a monoclonal antibody such as 2H5, 3D8 or 4H4) that has been immobilized on a solid support, commonly the well of a microtiter plate, with the biological sample, such that a soluble molecule naturally occurring in the sample and having an antigenic determinant that is reactive with the antibody is allowed to bind to the immobilized antibody (e.g., a 30 minute incubation time at room temperature is generally sufficient) to form an antigen-antibody complex or an immune complex. Unbound constituents of the sample are then removed from the immobilized immune complexes. Next, a second antibody specific for a HE4a antigen polypeptide is added, wherein the antigen combining site of the second antibody does not competitively inhibit binding of the antigen combining site of the immobilized first antibody to a HE4a polypeptide (e.g., a monoclonal antibody such as 2H5, 3D8 or 4H4 that is not the same as the monoclonal antibody immobilized on the solid support). The second antibody may be detectably labeled as provided herein, such that it may be directly detected. Alternatively, the second antibody may be indirectly detected through the use of a detectably labeled secondary (or "second stage") anti-antibody, or by using a specific detection reagent as provided herein. The subject invention method is not limited to any particular detection procedure, as those having familiarity with immunoassays will appreciate that there are numerous reagents and configurations for immunologically detecting a particular antigen (e.g., a mesothelin polypeptide) in a two-antibody sandwich immunoassay.

In certain preferred embodiments of the invention using the two-antibody sandwich assay described above, the first, immobilized antibody specific for a HE4a antigen polypeptide is a polyclonal antibody and the second antibody specific for a HE4a antigen polypeptide is a polyclonal antibody. In certain other embodiments of the invention the first, immobilized antibody specific for a HE4a antigen polypeptide is a monoclonal antibody and the second antibody specific for a HE4a antigen polypeptide is a polyclonal antibody. In certain other embodiments of the invention the first, immobilized antibody specific for a HE4a antigen polypeptide is a polyclonal antibody and the second antibody specific for a HE4a antigen polypeptide is a monoclonal antibody. In certain other highly preferred embodiments of the invention the first, immobilized antibody specific for a HE4a antigen polypeptide is a monoclonal antibody and the second antibody specific for a HE4a antigen polypeptide is a monoclonal antibody. For example, in these embodiments it should be noted that monoclonal antibodies 2H5, 3D8 and 4H4 as provided herein recognize distinct and noncompetitive antigenic determinants (e.g., epitopes) on HE4a polypeptides, such that any pairwise combination of these monoclonal antibodies may be employed. In other preferred embodiments of the invention the first, immobilized antibody specific for a HE4a antigen polypeptide and/or the second antibody specific for a HE4a antigen polypeptide may be any of the kinds of antibodies known in the art and referred to herein, for example by way of illustration and not limitation, Fab fragments, F(ab')$_2$ fragments, immunoglobulin V-region fusion proteins or single chain antibodies. Those familiar with the art will appreciate that the present invention encompasses the use of other antibody forms, fragments, derivatives and the like in the methods disclosed and claimed herein.

In certain particularly preferred embodiments, the second antibody may contain a detectable reporter moiety or label such as an enzyme, dye, radionuclide, luminescent group, fluorescent group or biotin, or the like. The amount of the second antibody that remains bound to the solid support is then determined using a method appropriate for the specific detectable reporter moiety or label. For radioactive groups, scintillation counting or autoradiographic methods are generally appropriate. Antibody-enzyme conjugates may be prepared using a variety of coupling techniques (for review see, e.g., Scouten, W. H., *Methods in Enzymology* 135:30-65, 1987). Spectroscopic methods may be used to detect dyes (including, for example, colorimetric products of enzyme reactions), luminescent groups and fluorescent groups. Biotin may be detected using avidin or streptavidin, coupled to a different reporter group (commonly a radioactive or fluorescent group or an enzyme). Enzyme reporter groups may generally be detected by the addition of substrate (generally for a specific period of time), followed by spectroscopic, spectrophotometric or other analysis of the reaction products. Standards and standard additions may be used to determine the level of mesothelin polypeptide in a sample, using well known techniques.

In another embodiment, the invention contemplates the use of a HE4a antigen polypeptide as provided herein to screen for the presence of a malignant condition by detection of immunospecifically reactive antibodies in a biological sample from a biological source or subject. According to this embodiment, a HE4a antigen polypeptide (or a fragment or variant thereof including a truncated HE4a antigen polypeptide as provided herein) is detectably labeled and contacted with a biological sample to detect binding to the HE4a antigen polypeptide of an antibody naturally occurring in soluble form in the sample. For example, the HE4a antigen polypeptide may be labeled biosynthetically by using the sequences disclosed herein in concert with well known methods such as incorporation during in vitro translation of a readily detectable (e.g. radioactively labeled) amino acid, or by using other detectable reporter moieties such as those described above. Without wishing to be bound by theory, this embodiment of the invention contemplates that certain HE4a polypeptides such as the HE4a fusion polypeptides disclosed herein, may provide peptides that are particularly immunogenic and so give rise to specific and detectable antibodies. For example, according to this theory certain HE4a fusion polypeptides may represent "non-self" antigens that provoke an avid immune response, while HE4a polypeptides that lack fusion domains may be viewed by the immune system as more resembling "self" antigens that do not readily elicit humoral or cell-mediated immunity.

As noted above, the present invention pertains in part to the surprising finding that soluble forms of HE4a antigen polypeptides occur naturally in subjects, including elevated levels of such soluble HE4a polypeptides in subjects having certain carcinomas.

A method of screening for the presence of a malignant condition according to the present invention may be further enhanced by the detection of more than one tumor associated marker in a biological sample from a subject. Accordingly, in certain embodiments the present invention provides a method of screening that, in addition to detecting reactivity of a naturally occurring soluble sample component with an antibody specific for a HE4a antigen polypeptide, also includes detection of at least one additional soluble marker of a malignant condition using established methods as known in the art and provided herein. As noted above, there are currently a number of soluble tumor associated antigens that are detectable in samples of readily obtained biological fluids. For example, certain embodiments of the invention relate to human mesothelin polypeptides, which include polypeptides such as the novel soluble mesothelin related antigen (MRA) polypeptide described in Scholler et al. (1999 *Proc. Nat. Acad. Sci. USA* 96:11531) and as also described in U.S. application Ser. No. 09/513,597.

As provided herein, a "mesothelin polypeptide" is a soluble polypeptide having an amino acid sequence that includes the peptide:

EVEKTACPSGKKAREIDES       SEQ ID NO:14 and further having at least one antigenic determinant reactive with at least one antibody having an antigen combining site that competitively inhibits the immunospecific binding of MAb K-1 (Chang et al., 1996 *Proc. Nat. Acad. Sci. USA* 93:136; MAb K-1 is available from, e.g., Signet Laboratories, Inc., Dedham, Mass.) or of monoclonal antibodies OV569, 4H3, 3G3 or 1A6 as provided in U.S. Ser. No. 09/513,597.

Thus, these additional soluble tumor associated antigens for use according to the present invention may include, but need not be limited to, mesothelin and mesothelin related antigen, CEA, CA125, sialyl TN, SCC, TPS and PLAP, (see e.g., Bast et al., 1983 *N. Eng. J. Med.* 309:883; Lloyd et al., 1997 *Int. J. Canc.* 71:842; Sarandakou et al., 1997 *Acta Oncol.* 36:755; Sarandakou et al., 1998 *Eur. J. Gynaecol. Oncol.* 19:73; Meier et al., 1997 *Anticanc. Res.* 17(4B): 2945; Kudoh et al., 1999 *Gynecol. Obstet. Invest.* 47:52; Ind et al., 1997 *Br. J. Obstet. Gynaecol.* 104:1024; Bell et al. 1998 *Br. J. Obstet. Gynaecol.* 105:1136; Cioffi et al., 1997 *Tumori* 83:594; Meier et al. 1997 *Anticanc. Res.* 17(4B): 2949; Meier et al., 1997 *Anticanc. Res.* 17(4B):3019) and may further include any known marker the presence of which in a biological sample may be correlated with the presence of at least one malignant condition, as provided herein.

Alternatively, nucleic acid sequences encoding HE4a polypeptides may be detected, using standard hybridization and/or polymerase chain reaction (PCR) techniques. Suitable probes and primers may be designed by those of ordinary skill in the art based on the HE4a cDNA sequences provided herein. Assays may generally be performed using any of a variety of samples obtained from a biological source, such as eukaryotic cells, bacteria, viruses, extracts prepared from such organisms and fluids found within living organisms.

The following Examples are offered by way of illustration and not by way of limitation.

EXAMPLES

Example 1

Real-Time PCR Detection of HE4A Expression in Human Samples

One hundred and fifty-eight human tissue biopsies, or RNA samples from biopsies, were obtained according to the procedures approved by the institutional review boards of the University of Washington, Swedish Hospital and Fred Hutchinson Cancer Research Center, all of Seattle, Wash. Samples from normal tissues (adrenal gland, bone marrow, brain, colon, endometrium, stomach, heart, kidney, liver, lung, lung, mammary gland, skeletal muscle, skeletal muscle, myometrium, peripheral nerve, peripheral blood lymphocyte preparations, salivary gland, skin, small intestine, spinal cord, spleen, spleen, trachea, thymus, uterus, peripheral blood lymphocyte cluture, and 40 normal ovaries), from benign ovarian lesions (13 serous cystadenomas), from 2 ovarian tumors of borderline malignancy, from 3 stage I mucinous ovarian carcinomas, 3 stage I serous ovarian carcinomas, 37 stage III serous ovarian carcinomas, 7 stage IV serous ovarian carcinomas, 6 samples of tissue from metastatic ovarian carcinoma, and 2 tubes from women with ovarian cancers were included. All tissue samples were obtained from women prior to therapy, and a portion of each tumor was immediately placed in liquid nitrogen, with the remainder of the specimen submitted for routine histology. Only those samples which on histopathologic examination were found to be composed of more than 80% tumor cells, and which were without necrosis, were used for hybridization and real time PCR experiments. RNA from an ovarian surface epithelial culture (OSE, obtained from B. Karlan, Cedars Sinai Hospital, Los Angeles, Calif.), and three additional OSE samples (obtained from R. Hernandez, University of Washington, Seattle, Wash.) were also included. In all, 151 (94 nonmalignant tissues and 57 cancers) were reserved for realtime quantitative PCR confirmation of overexpression of genes of interest, including HE4a as described below.

Real-time quantitative PCR was performed as follows. The HE4 realtime PCR primers were:

```
AGCAGAGAAGACTGGCGTGT (forward)     [SEQ ID NO:15]
and
GAAAGGGAGAAGCTGTGGTCA (reverse).   [SEQ ID NO:16]
```

These primers generated a PCR product of 427 bp length. Total RNA was reverse transcribed using oligo-dT primer and Superscript II Reverse Transcriptase (Life Technologies, Inc., Bethesda, Md.) as specified by the manufacturer. Real-time quantitative PCR was performed using an ABI7700 machine (PE Biosystems, Foster City, Calif.) and the SYBR-Green protocol. Five duplicates of a 2-fold serial dilution of a white blood cell cDNA preparation served as a template for the amplification of the standard (S31iii125, which in previous experiments was demonstrated to be universally expressed in normal and malignant tissues, see Schummer et al., 1999 Gene 1999).

GenBank accession number: U61734, forward primer:

```
forward primer:  CGACGCTTCTTCAAGGCCAA, SEQ ID NO:17
reverse primer:  ATGGAAGCCCAAGCTGCTGA. SEQ ID NO:18
```

The negative controls consisted of total RNA from an ovarian carcinoma which was reverse transcribed without the enzyme and one well containing all components of the PCR without any template. All runs were performed in duplicate. Each run was analyzed on an agarose gel for the presence of a single PCR band to eliminate artifactual bands. The results for each 96-well plate were analyzed using software (Sequence Detector™) provided by the manufacturer of the PCR machine; this analysis permits determinatiaon of expression levels of a nucleic acid sequence of interest (HE4a) relative to the standard.

Figure 1B:
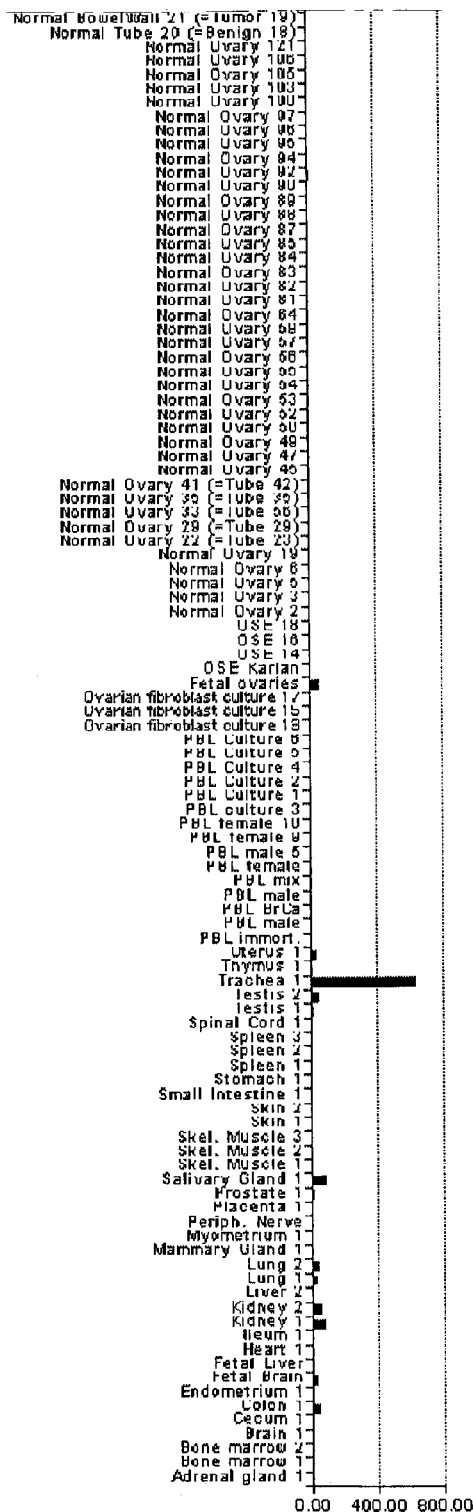

The expression values, as shown in FIG. 1, were depicted in arbitrary units relative to the internal standard and did not reflect absolute quantities of mRNA molecules in standard units of measure. Based on the amplitude of the mean HE4a expression levels and comparison of these values to those of other known genes (notably beta actin as a highly expressed gene), FIG. 1 shows that transcripts encoding HE4a were expressed at moderate-to-high relative levels.

Example 2

Cloning and Expression of Nucleic Acid Sequences Encoding HE4A

Amplification of HE4a fusion construct cDNA from high throughput HE4a cDNA clone: The cDNA sequence for HE4 (SEQ ID NO:8) as originally published by Kirchoff et al., (1991) was deposited in GenBank Accession # X63187 and provided the basis for oligonucleotide primer design to clone cDNA encoding HE4a (SEQ ID NO:10), as described herein. The cDNA for HE4a, identified and isolated as a differentially expressed gene product using high throughput cDNA arrays, was cloned in pSPORT as an 840 base pair fragment. This cDNA was used as template in PCR reactions to amplify HE4a in a form appropriate for creating synthetic fusion protein genes, as described in this Example.

A portion of the HE4 coding sequence (SEQ ID NO:8) appeared to encode a presumed secretory signal peptide; therefore, this native leader peptide was used in initial constructs to preserve as much of the molecule's structure as possible. In addition, because HE4a was relatively small and the sequence did not contain any unusual structural features such as transmembrane domains or cytoplasmic targeting sequences, a fusion protein was designed that incorporated the complete HE4a gene product fused to the human IgG1 Fc domain. Primers were designed that encoded appropriate restriction sites for cloning and created the necessary in-frame fusions of protein domains for the final construct. The 5' primer (SEQ ID NO:1, or HE4-5') was a 39-mer that included a HindIII site, a Kozak sequence to improve expression adjacent to the first ATG, and a portion of the HE4a leader peptide based on the previously published HE4 sequence. The 3' primer (SEQ ID NO:2, or HE4-3'-1) was a 36-mer that included an in-frame BamHI site for fusion to the human-Ig tail cDNA, with the 3' end of the HE4 coding sequence truncated just before the STOP codon. PCR amplification reactions were performed using these two primers at 50 pmol and 1 ng HE4/pSPORT plasmid as template. Fifty microliter reactions also included 2.5 units (0.5 ml) ExTaq DNA polymerase (TaKaRa Shuzo Biomedical, Otsu, Shiga, Japan), diluted buffers and nucleotides according to package insert directions. Reactions were amplified for 30 cycles, with an amplification profile of 94° C., 30 seconds, 60° C., 30 seconds, and 72° C., 30 seconds. PCR products of the expected size (approximately 400 base pairs) for the full length HE4 were obtained.

Figure 2:
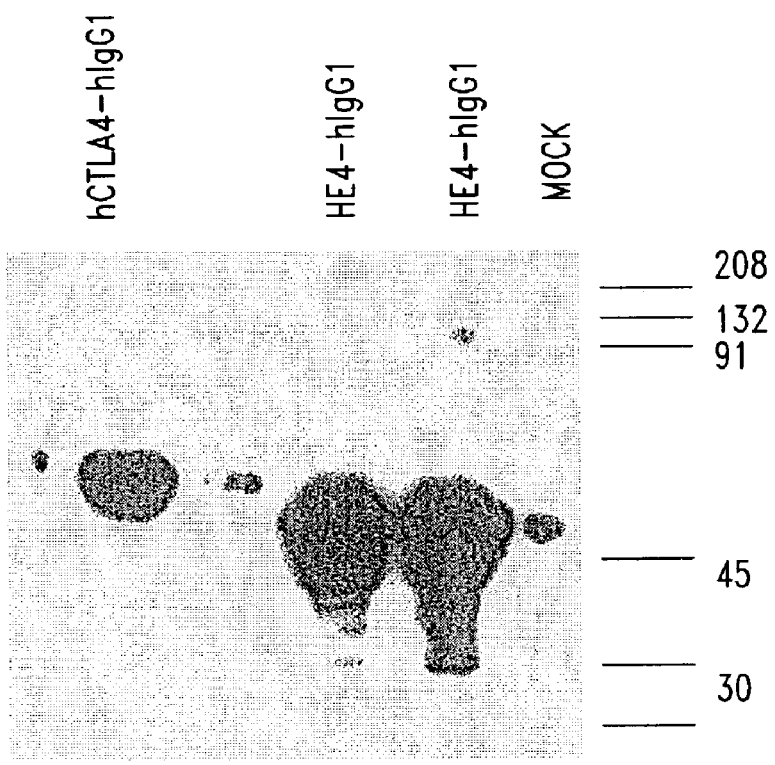
FIG. 2 shows western blot analysis of expressed HE4a fusion proteins.

These fragments were restriction digested, purified, and ligated into the appropriately digested mammalian expression plasmid already containing the human IgG1 insert. Ligation products were transformed into DH5α bacterial cells and transformants screened for the presence of HE4-hIgG1 fusion gene inserts. Plasmid DNA from several isolates was then sequenced using the BigDye Terminator Cycle Sequencing Kit (PE Biosystems, Foster City, Calif.) on an ABI Prism 310 (PE Biosystems) sequencer. In addition, plasmid DNA from these isolates was also transfected by DEAE-Dextran transient transfections of COS7 cells as described (Hayden et al., 1994 *Ther. Immunol.* 1:3). Culture supernatants were harvested after 72 h and screened by immunoprecipitation with protein A-agarose, reducing SDS-PAGE electrophoresis, and Western blotting (FIG. 2). Western blots were probed using a goat anti-human IgG conjugate at 1:5000, followed by ECL development.

Results from the sequence analysis indicated that the HE4a coding sequence obtained (SEQ ID NO:10) and the deduced amino acid sequence (SEQ ID NO:11) differed from the published HE4 coding (SEQ ID NO:8) and translated (SEQ ID NO:9) sequences at several positions. Sequences were therefore also obtained from cDNAs derived from normal human epididymis and from several tumor cell lines and primary tumor RNA, and the HE4a coding sequence as set forth in SEQ ID NO:10, and the deduced encoded amino acid sequence set forth in SEQ ID NO:11, were confirmed.

Cloning HE4 cDNA from Tumor Cell Lines: RNA was prepared from several ovarian tumor cell lines, including 4007 and OVCAR3 (see, e.g., Hellstrom et al., 2001 *Canc. Res.* 61:2420), using Trizol (Life Technologies, Gaithersburg, Md.) according to the manufacturer's instructions. cDNA was prepared using 1-3 μg RNA, random hexamers, and Superscript II Reverse Transcriptase (Life Technologies) according to manufacturer's directions. HE4 cDNA was PCR amplified from the random primed cDNA in 50 μl reactions containing 1 μg cDNA, 2.5 units (0.5 ml) ExTaq DNA polymerase (TaKaRa Shuzo Biomedical, Otsu, Shiga, Japan), diluted buffers and nucleotides according to insert directions, and HE4-5' and HE4-3'-1 specific primers. Reactions were amplified for 30 cycles, with an amplification profile of 94° C., 30 seconds, 60° C., 30 seconds, and 72° C., 30 seconds. The HE4-5' and HE4-3 oligonucleotides were again used for PCR amplification of HE4 from the tumor derived cDNAs. PCR products of the expected size for the full length HE4 were obtained and the fragments were cloned into pT-AdvanTAge vectors (Clontech, Palo Alto, Calif.) for sequence analysis. Clones with inserts were sequenced as described above, and the PCR fragments from the tumor RNA samples were found to encode HE4a sequence identical to the original clones described above; these HE4a sequences differed from the published sequence for HE4 (Kirchhoff et al., 1991). Similarly, HE4a coding sequence was obtained from normal epidymis (SEQ ID NO:10) and from primary tumor tissue cDNAs (SEQ ID NO:12), and thus matched the new HE4a sequence desribed above but differed from the HE4 sequence (SEQ ID NO:8) of Kirchoff et al. (1991).

Production of HE4Ig fusion protein. The HE4-hIgG1 cDNA construct (SEQ ID NO:7) was inserted as a HindIII-XbaI fragment into the multiple cloning site of the mammalian expression vector pD18, a derivative of pCDNA 3 as described previously (Hayden et al., 1996 *Tissue Antigens* 48: 242). Constructs initially were transfected by DEAE-Dextran transient transfections as described (Hayden, et al., 1994 *Ther. Immunol.* 1: 3). Plasmid DNA from several isolates was prepared and used to transiently transfect COS7 cells. Culture supernatants were harvested after 72 h and screened by immunoprecipitation with protein A-agarose, reducing SDS-PAGE electrophoresis, and Western blotting (FIG. 2).

CHO-DG44 cells (Urlaub et al. 1986 *Somat. Cell. Mol. Genet.* 12: 55) were used to construct stable lines expressing high levels of the fusion proteins of interest. Stable CHO lines expressing HE4Ig were created by high copy electroporation in the pD18 vector (Hayden et al., 1996 *Tissue Antigens* 48: 242; Barsoum, 1990 *DNA Cell Biol.* 9: 293) and selection of methotrexate-resistant clones by limiting dilution in Excell 302 CHO media (JRH Biosciences, Denver, Pa.) containing recombinant insulin (Life Technologies, Gaithersburg, Md.), sodium pyruvate (Irvine Scientific, Santa Ana, Calif.), glutamine (Irvine Scientific), 2× non-essential amino acids for MEM (Irvine Scientific) and 100 nM methotrexate (Sigma, St. Louis, Mo.). Culture supernatants from resistant clones were then assayed by IgG sandwich ELISA to screen for high producing lines. Spent supernatants were harvested from large-scale cultures and HE4Ig was purified by protein A affinity chromatography over a 2-ml protein A-agarose (Repligen, Cambridge, Mass.) column. Fusion protein was eluted from the column as 0.8-ml fractions in 0.1 M citrate buffer (pH 2.7), and neutralized using 100 μl of 1 M Tris base (pH 10.5). Eluted fractions were assayed for absorbance at 280 nm, and fractions containing fusion protein were pooled, dialyzed overnight in several liters of PBS (pH 7.4), and filter sterilized through 0.2-μm syringe filter units (Millipore, Bedford, Mass.).

Stable transfectants were used to produce enough protein for immunization of BALB/c mice. Mice were initially injected intraperitoneally (IP) with 10 micrograms of purified HE4-hIgG1 fusion protein at 4 week intervals. After a primary injection and two boosts using this immunization protocol, mice were subsequently injected with 10 μg protein plus TiterMax Gold adjuvant IP and then SC for two more boosts prior to harvest of spleens. Hybridomas were made by fusing spleen cells from immunized mice with the myeloma partner P3-X63-Ag8-653.

Western analysis of HE4Ig fusion proteins. Protein samples were resolved by SDS-PAGE electrophoresis on a 10% Tris/Bis NOVEX gel (Invitrogen, San Diego Calif.), and transferred by semi-dry blotting onto PVDF membranes (Millipore). The membranes were blocked to prevent non-specific antibody binding by incubation in 5% nonfat dry milk (Carnation) in PBS/0.25% NP-40 or TBS-T (50 mM Tris HCl, pH 7.6, 0.15 M NaCl, and 0.05% Tween-20) overnight at 4° C. The membranes were incubated with HRP-goat anti-human IgG (1/10,000) or with HRP-Streptavidin (1:5000) (Caltag) in TBS-T for 1 h at room temperature or 4° C., with gentle agitation. After two rinses and four washes with TBST, the membrane was incubated in ECL™ (Amersham, Little Chalfont, UK) reagent for 60 s and exposure to autoradiography film for visualization of the bands (FIG. 2). Fusion protein samples were harvested from culture supernatants or from protein A eluates of purified samples and protein A precipitated using 50 μl protein A agarose (Repligen, Cambridge, Mass.). Immuneprecipitates were washed and resuspended in SDS-PAGE reducing sample loading buffer, boiled, then resolved by SDS-PAGE electrophoresis on a 10% Tris/Bis NOVEX gel (Invitrogen, San Diego Calif.), and transferred by semi-dry blotting onto PVDF membranes (Millipore). The membranes were blocked to prevent nonspecific antibody binding by incubation in 5% nonfat dry milk (Carnation) in PBS/0.25% NP-40 or TBS-T (50 mM Tris HCl, pH 7.6, 0.15 M NaCl, and 0.05% Tween-20) from 1 hour to overnight at 4° C. The membranes were incubated with HRP-goat anti-human IgG (1/10,000), washed in TBS-T, and exposed to ECL™ (Amersham, Little Chalfont, UK) reagent for 60 s. ECL-blots were then exposed to autoradiography film for visualization of the bands. FIG. 2, Lane 1 contained immunoprecipitated samples from supernatant of CTLA4-hIgG1 transfected COS7 cells, Lanes 3 and 4 contained HE4-hIgG1 fusion protein culture supernatants, and Lane 5 contained mock transfected COS supernatant. The HE4-hIgG1 fusion protein rans at an apparent Mr of approximately 48 kDa on reduced gels or Western blots, larger than the 39 kDa expected based on the predicted amino acid sequence, suggesting that the molecule was glycosylated.

Construction and Expression of HE4-mIgG2a Fusion Proteins: A similar construction to the HE4-hIgG1 fusion gene was also made, but substituting the murine-IgG2a domain for the human IgG Fe fragment. The alternate tail was used so that immunizations of mice would not be affected by immunogenicity of the human Ig tail fusion domain. Existing cDNA clones of the mIgG2a tail were out of frame with respect to the HE4a clone described above, so the -mIgG2a cassette was reamplified from such plasmids to create an in-frame fusion domain. The forward, sense primer used was mIgG2aBAMIF:

[SEQ ID NO:19]
5'-gttgtcggatccgagcccagagggcccacaatcaag-3', while the reverse, antisense primer was designated mIgG2a3'Xba+S:

[SEQ ID NO:20]
5'-gttgtttctagattatcatttacccggagtccgggagaagctc-3'.

The template used contained murine CTLA4 fused to the murine IgG2a Fe domain, but with the restriction site at the fusion junction out of frame with respect to the codon spacing. The new oligonucleotides created a frameshift, altering the reading frame at the BamHI site so that the fusion gene with HE4 would result in expression of a complete HE4-mIgG2a fusion protein. PCR products were amplified, subcloned, and processed as described for the human fusion genes. Molecules were subcloned into the pD18 mammalian expression vector, stable CHO clones generated, and fusion protein expressed as described above for the HE4-human IgG1 fusion proteins.

Example 3

Monoclonal Antibodies Specific for HE4A

Figure 3:
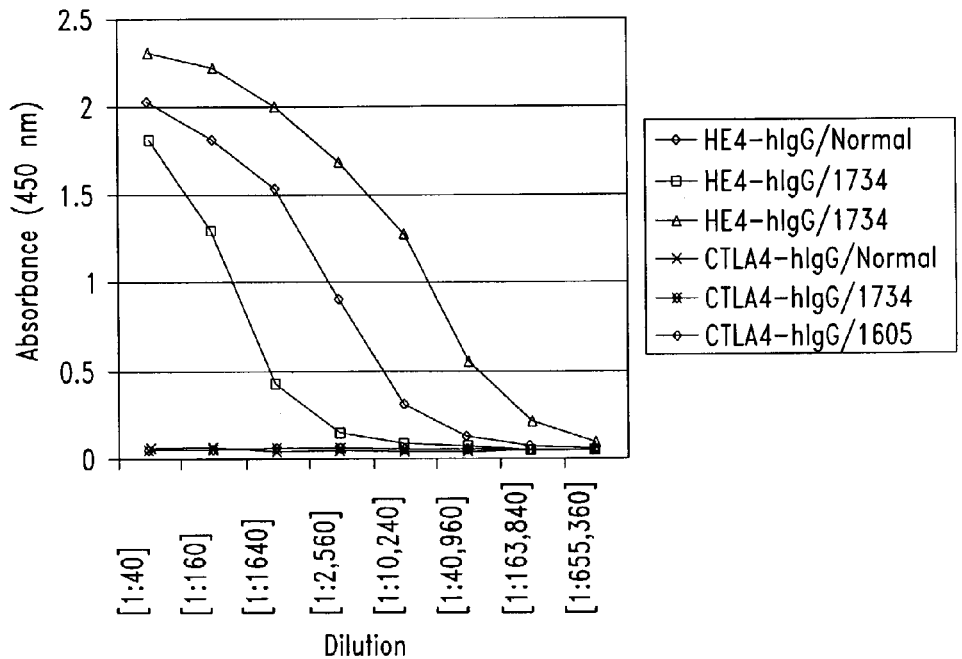
FIG. 3 depicts detection of antibodies reactive with HE4a-mIg fusion protein in sera from two immune mice (1605 and 1734) by ELISA.

Generation of anti-HE4a Mabs. In initial experiments, several BALB/c mice were immunized with HE4a-hIgG fusion proteins prepared as described above, with and without adjuvant. Although high antibody titers were seen in these mice, the antibodies were not specific for HE4a, since equally high titers were seen against a control fusion protein having the hIgG tail (CTLA4-hIg fusion). Therefore, HE4a-mIgG fusion protein was used for immunization. FIG. 3 illustrates the results from two immunizations that led to high titered antibodies against HE4a in two BALB/c mice (1605 and 1734) that were each twice immunized with HE4a-mIgG plus adjuvant (TiterMax®, CytRx Corp., Norcross, Ga.) according to the manufacturer's instructions, given subcutaneously in the tail. HE4a-specific hybridomas were prepared by standard methodologies using spleen cells from mice exhibiting high HBE4a-specific antibody titers. FIG. 4 shows the initial testing, by ELISA, of hybridomas made by using spleen cells from mouse 1605 (whose serum data are shown in FIG. 3). Three wells displayed high reactivity against HE4a-hIg. Three hybridomas, 2H5, 3D8 and 4H4, were subsequently isolated from these wells following cloning by limiting dilution. Hybridomas 2H5 and 3D8 were found to identify different epitopes according to competition assays.

Figure 5:
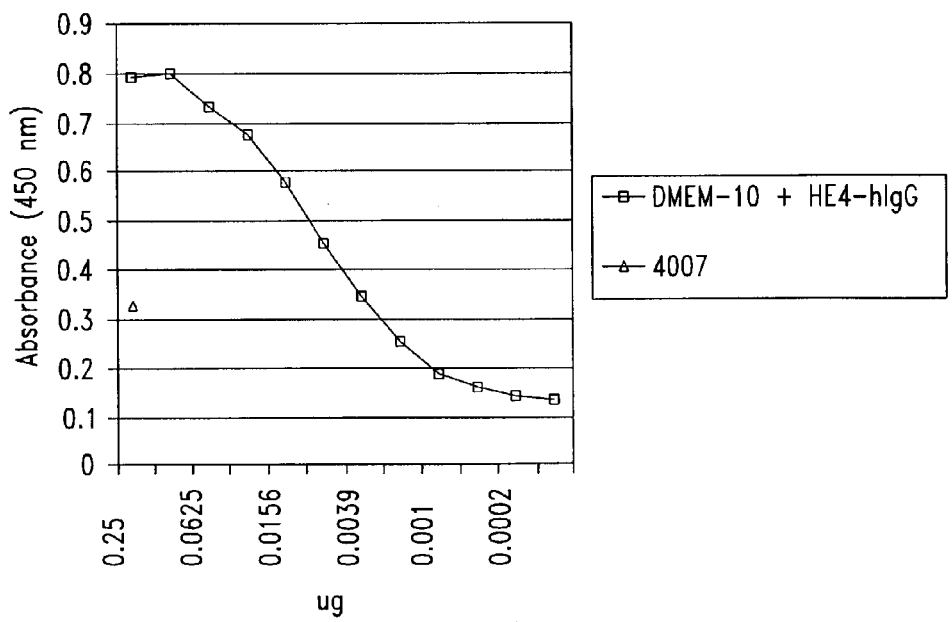
FIG. 5 shows detection of HE4a-hIgG fusion protein by double-determinant sandwich ELISA using immobilized HE4a-specific monoclonal antibody 3D8 as the capture reagent and biotinylated HE4a-specific monoclonal antibody 2H5 as the detection reagent. Also shown is detection of soluble HE4a in supernatant fluid from ovarian carcinoma cell line 4007 (Δ).
Figure 6:
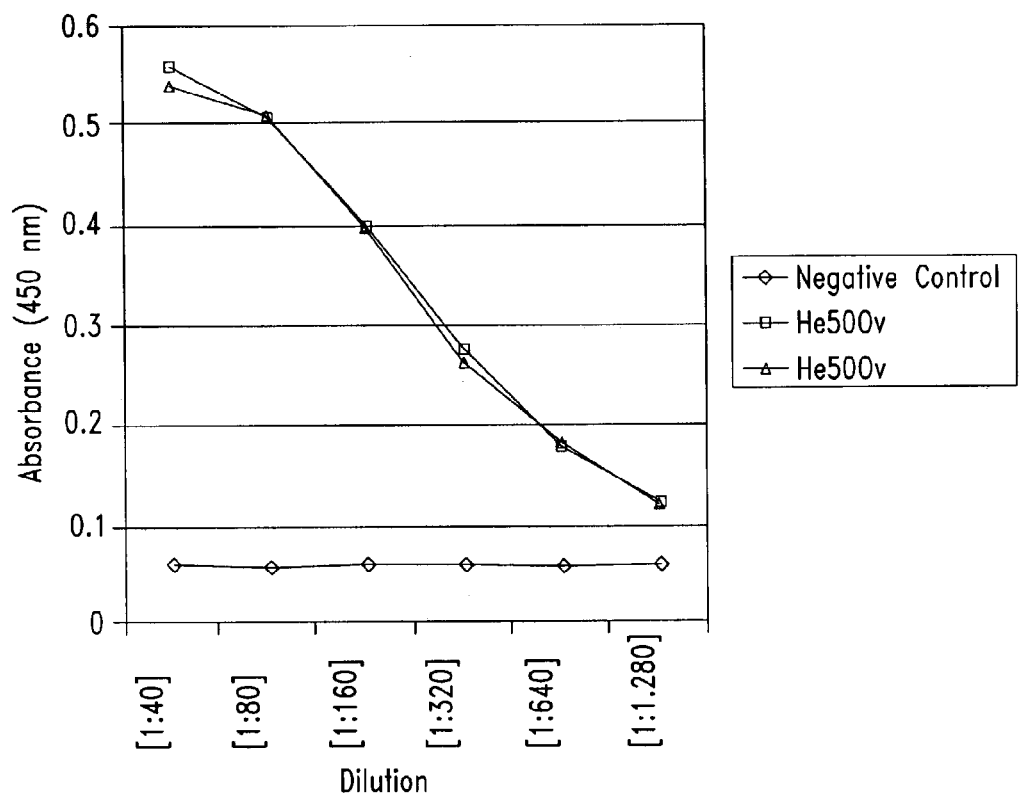
FIG. 6 shows detection by sandwich ELISA of HE4a antigen in serially diluted ascites fluid from an ovarian carcinoma patient.

Construction and application of an ELISA for tumor diagnosis. A double determinant ("sandwich") ELISA was constructed, using a similar approach as that employed to make an ELISA which measures mesothelin/MPF and related antigens in serum and other fluids (Scholler et al., Proc. Natl. Acad. Sci. USA 96, 11531, 1999) using the two MAbs 2H5 and 3D8 referred to above. FIG. 5 shows an example of a standard curve, prepared by using HE4a-hIgG diluted in DMEM culture medium. As illustrated in the figure, a signal was detected at the 1 ng level of HE4a-hIgG. FIG. 5 also shows that undiluted culture medium from an ovarian carcinoma line (4007) gave a detectable signal. FIG. 6 shows that ascites fluid from a patient (designated OV50) diagnosed with ovarian carcinoma contained HE4a antigen which was still detectable at the highest dilution tested (1:1280).

The initial HE4a ELISA was improved by establishing the optimal amounts of the two antibodies used. One of these antibodies, 2H5, was biotinylated and the other antibody, 3D8 was immobilized by permitting it to become bound to the bottom of the test plate; the respective doses of the two monoclonal antibodies for the assay were 2.5 and 100 μg/ml. Except for the different Mabs and doses of the Mabs being used, as just noted, the assay methods were identical to those described for mesothelin/MPF and related molecules (Scholler et al., 1999 Proc. Natl. Acad. Sci. USA 96:11531).

Preliminary testing of sera from patients with ovarian carcinoma and a variety of controls indicated that the HE4a protein was elevated in a significant fraction of patients with ovarian carcinoma, including patients with early disease, and not in control sera for which the background is very low. In a study using the above described sandwich ELISA assay and coded serum samples from approximately 400 patients (provided by Swedish Hospital, Seattle, Wash.), all samples from patients diagnosed with ovarian cancer were correctly scored as positive by the HE4a ELISA, which further predicted no false positives. It is therefore contemplated, without wishing to be bound by theory, that assaying for HE4a protein in sera and other body fluids may thereby provide a clinically beneficial complement to existing diagnostic assays for ovarian carcinoma (such as CA125). Furthermore, although the ELISA has so far been investigated with respect to its ability to aid the diagnosis of ovarian carcinoma, it should be equally applicable to any tumor that overexpresses the HE4a encoded antigen. The same ELISA, or a modification of it, should also be applicable for studies of HE4-related molecules, if future studies will identify such.

Expression of HE4 protein at the cell surface. Studies performed with flow cytometry, using ovarian carcinoma cell lines with a B cell line as a negative control, showed that the HE4a encoded antigen was expressed at the cell surface among some ovarian carcinomas. The cell lines used and the flow cytometry technique employed have been previously described (Hellstrom et al., 2001 *Cancer Res.* 61, 2420). For example, 93% of OVCAR 3 cells were positive, as were 71% of cells from ovarian cancer line 4010 and 38% of cells from ovarian cancer line HE50 OV, while less than 20% of cells were positive from another 10 ovarian carcinoma lines tested. This suggested that HE4a antigen at the cell surface may, according to non-limiting theory, provide a target for immunotherapeutic strategies such as HE4a-specific antibody-mediated and/or HE4a-specific T-cell mediated therapies.

Example 4

Prophylactic and Therapeutic Vaccines Targeting HE4A Epitopes

Detection of the amplification of HE4a-encoding nucleic acid sequences and/or of HE4a overexpression in certain tumors (particularly malignant ovarian tumors) is performed employing the compositions and methods described above, and HE4a expression levels are compared to those in normal tissues. The increased occurrence of HE4a-specific monoclonal antibody-defined epitopes in tumors provides for the identification of HE4a epitopes that are used as targets for prophylactic or preventive vaccines with applicability in cancer therapy; such vaccines may also usefully alter (e.g., increase or decrease in a statistically significant manner relative to a suitable control) fertilization (which may in certain embodiments be reflected by demonstration of HE4a protease-inhibitory or protease-enhancing activity using well known assays for protease inhibition by members of the four-disulfide core family, such as Slp-1). A large variety of approaches to make vaccines has been identified and described in many review articles (e.g., by Hellstrom and Hellstrom, In *Handbook in Experimental Pharmacology*, vol. "Vaccines", Springer, Heidelberg, p. 463, 1999). These include, but are not restricted to, the use of proteins, fusion proteins and peptides, DNA plasmids, recombinant viruses, anti-idiotypic antibodies, dendritic cells pulsed with peptide epitopes in vitro, and anti-idiotypic antibodies. The vaccines may be used alone or in combinations with adjuvants, and/or lymphokines, such as GMCSF. According to non-limiting theory, detection of circulating soluble HE4a proteins as desribed above would not be expected to interfere with the use of vaccines inducing T cell-mediated immunity, since the T cells recognize epitopes presented in the context of MHC molecules on cell surfaces but do not react to circulating antigen or immune complexes.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of screening for the presence of an ovarian carcinoma in a subject comprising: contacting a biological sample from a subject with at least one antibody specific for an HE4a antigen polypeptide, the polypeptide having an amino acid sequence comprising SEQ ID NO: 11, to determine the presence in the biological sample of a molecule naturally occurring in soluble form in the sample and having an antigenic determinant that is reactive with the antibody, under conditions and for a time sufficient to detect binding of the antibody to the antigenic determinant, and therefrom detecting the presence of an ovarian carcinoma, wherein the biological sample is selected from the group consisting of blood, serum, plasma, ascites fluid, and peritoneal fluid.

2. The method of claim 1 wherein the biological sample is serum.

3. The method of claim 1 wherein the biological sample is plasma.

4. The method of claim 1 wherein the biological sample is ascites fluid.

5. The method of claim 1 wherein the antibody comprises a polyclonal antibody.

6. The method of claim 1 wherein the antibody comprises an affinity purified antibody.

7. The method of claim 1 wherein the antibody comprises a monoclonal antibody.

8. The method of claim 1 wherein the antibody comprises a recombinant antibody.

9. The method of claim 1 wherein the antibody comprises a chimeric antibody.

10. The method of claim 1 wherein the antibody comprises a humanized antibody.

11. The method of claim 1 wherein the antibody comprises a single chain antibody.

12. The method of claim 1 wherein detection of binding of the antibody to an antigenic determinant comprises detection of a radionuclide.

13. The method of claim 1 wherein detection of binding of the antibody to an antigenic determinant comprises detection of a fluorophore.

14. The method of claim 1 wherein detection of binding of the antibody to an antigenic determinant comprises detection of a binding event between an avidin molecule and a biotin molecule.

15. The method of claim 1 wherein detection of binding of the antibody to an antigenic determinant comprises detection of a binding event between a streptavidin molecule and a biotin molecule.

16. The method of claim 1 wherein detection of binding of the antibody to an antigenic determinant comprises spectrophotometric detection of a product of an enzyme reaction.

17. The method of claim 1 wherein the antibody is detectably labeled.

18. The method of claim 1 wherein the antibody is not detectably labeled and wherein detection of binding of the antibody to an antigenic determinant is indirect.

19. A method of screening for the presence of an ovarian carcinoma in a subject comprising: contacting a biological sample comprising a cell from a subject with at least one antibody specific for an HE4a antigen polypeptide, the polypeptide having an amino acid sequence comprising SEQ ID NO: 11, to determine the presence in the biological sample of a cell surface molecule having an antigenic determinant that is reactive with the antibody, under conditions and for a time sufficient to detect binding of the antibody to the antigenic determinant, and therefrom detecting the presence of an ovarian carcinoma, wherein the biological sample is selected from the group consisting of blood, serum, plasma, ascites fluid, and peritoneal fluid.

20. The method of claim 19 wherein the biological sample is serum.

21. The method of claim 19 wherein the biological sample is plasma.

22. The method of claim 19 wherein the biological sample is ascites fluid.

23. The method of claim 19 wherein the antibody comprises a polyclonal antibody.

24. The method of claim 19 wherein the antibody comprises an affinity purified antibody.

25. The method of claim 19 wherein the antibody comprises a monoclonal antibody.

26. The method of claim 19 wherein the antibody comprises a recombinant antibody.

27. The method of claim 19 wherein the antibody comprises a chimeric antibody.

28. The method of claim 19 wherein the antibody comprises a humanized antibody.

29. The method of claim 19 wherein the antibody comprises a single chain antibody.

30. The method of claim 19 wherein detection of binding of the antibody to an antigenic determinant comprises detection of a radionuclide.

31. The method of claim 19 wherein detection of binding of the antibody to an antigenic determinant comprises detection of a fluorophore.

32. The method of claim 19 wherein detection of binding of the antibody to an antigenic determinant comprises detection of a binding event between an avidin molecule and a biotin molecule.

33. The method of claim 19 wherein detection of binding of the antibody to an antigenic determinant comprises detection of a binding event between a streptavidin molecule and a biotin molecule.

34. The method of claim 19 wherein detection of binding of the antibody to an antigenic determinant comprises spectrophotometric detection of a product of an enzyme reaction.

35. The method of claim 19 wherein the antibody is detectably labeled.

36. The method of claim 19 wherein the antibody is not detectably labeled and wherein detection of binding of the antibody to an antigenic determinant is indirect.

37. A method of screening for the presence of an ovarian carcinoma in a subject comprising: contacting a biological sample from a subject with at least one antibody specific for a HE4a antigen polypeptide, the polypeptide having an amino acid sequence comprising SEQ ID NO: 11, to determine the presence in the biological sample of a molecule selected from the group consisting of (i) a molecule naturally occurring in soluble form in the sample, and (ii) a cell surface molecule wherein the sample comprises a cell from the subject, the molecule having an antigenic determinant that is reactive with the antibody, under conditions and for a time sufficient to detect binding of the antibody to the antigenic determinant, wherein the antibody immunospecifically binds to HE4a antigen, and therefrom detecting the presence of an ovarian carcinoma, wherein the biological sample is selected from the group consisting of blood, serum, plasma, ascites fluid, and peritoneal fluid.

38. A method of screening for the presence of an ovarian carcinoma in a subject comprising: contacting a biological sample from a subject with at least one immobilized first antibody specific for a HE4a antigen polypeptide, the polypeptide having an amino acid sequence comprising SEQ ID NO: 11, to determine the presence in the biological sample of a molecule naturally occurring in soluble form in the sample, under conditions and for a time sufficient to specifically bind the immobilized first antibody to the HE4a antigen polypeptide and thereby form an immune complex; removing constituents of the sample that do not specifically bind to the immobilized first antibody; and contacting the immune complex with at least one second antibody specific for a HE4a antigen polypeptide, wherein the antigen combining site of the second antibody does not competitively inhibit the antigen combining site of the immobilized first antibody, under conditions and for a time sufficient to detect specific binding of the second antibody to the HE4a antigen polypeptide, and therefrom detecting the presence of an ovarian carcinoma, wherein the biological sample is selected from the group consisting of blood, serum, plasma, ascites fluid, and peritoneal fluid.

39. A method of screening for the presence of an ovarian carcinoma in a subject comprising: contacting each of (i) a first biological, sample from a first subject suspected of having an ovarian carcinoma, and (ii) a second biological sample from a second subject known to be free of an ovarian carcinoma, with at least one antibody specific for a HE4a antigen polypeptide, the polypeptide having an amino acid sequence comprising SEQ ID NO: 11, to determine the presence in each of the first and second biological samples of a molecule selected from the group consisting of (i) a molecule naturally occurring in soluble form in the sample, and (ii) a cell surface molecule wherein the first and second biological samples each comprise, respectively, a cell from the first and second subjects, the molecule having an antigenic determinant that is reactive with the antibody, under conditions and for a time sufficient to detect binding of the antibody to the antigenic determinant, and comparing a level of detectable binding of the antibody to the antigenic determinant in the first biological sample to a level of detectable binding of the antibody to the antigenic determinant in the second biological sample, and therefrom detecting the presence of an ovarian carcinoma, wherein each of the first and second biological samples is selected from the group consisting of blood, serum, plasma, ascites fluid, and peritoneal fluid.

40. A method of screening for the presence of an ovarian carcinoma in a subject comprising: detecting in a biological sample from the subject the presence of an antibody that immunospecifically binds to a HE4a antigen polypeptide, the polypeptide having an amino acid sequence comprising SEQ ID NO: 11, wherein the biological sample is selected from the group consisting of blood, serum, plasma, ascites fluid, and peritoneal fluid.

41. A method of screening for the presence of an ovarian carcinoma in a subject comprising: contacting a biological sample from a subject with a detectably labeled HE4a polypeptide, the polypeptide having an amino acid sequence comprising SEQ ID NO: 11, under conditions and for a time sufficient to detect binding to the HE4a polypeptide of an antibody naturally occurring in soluble form in the sample, and therefrom detecting the presence of an ovarian carcinoma, wherein the biological sample is selected from the group consisting of blood, serum, plasma, ascites fluid, and peritoneal fluid.

42. The method of any one of claims 1, 19, 2-4, 5-8, 37, 38, 20-22, and 23-36, further comprising determining the presence in the sample of at least one soluble marker of a malignant condition selected from the group consisting of a mesothelin related antigen, carcinoembryonic antigen, CA125, sialyl TN, squamous cell carcinoma antigen, tissue polypeptide antigen, and placental alkaline phosphatase.

* * * * *